US006727279B2

(12) United States Patent
Mittendorf et al.

(10) Patent No.: US 6,727,279 B2
(45) Date of Patent: Apr. 27, 2004

(54) ARYLSULPHONAMIDES AND ANALOGUES

(75) Inventors: Joachim Mittendorf, Wuppertal (DE); Jürgen Dressel, Radevormwald (DE); Michael Matzke, Wuppertal (DE); Jörg Keldenich, Wuppertal (DE); Frank Mauler, Overath (DE); Jean-Marie-Victor de Vry, Rösrath (DE); Jürgen Franz, Witten (DE); Peter Spreyer, Düsseldorf (DE); Verena Vöhringer, Wuppertal (DE); Joachim Schumacher, Wuppertal (DE); Michael-Harold Rock, Hvidovre (DK); Ervin Horvàth, Leverkusen (DE); Arno Friedl, Bergisch Gladbach (DE); Klaus-Helmut Mohrs, Wuppertal (DE); Siegfried Raddatz, Köln (DE); Reinhard Jork, Haan (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/225,823

(22) Filed: Aug. 21, 2002

(65) Prior Publication Data

US 2003/0073727 A1 Apr. 17, 2003

Related U.S. Application Data

(63) Continuation of application No. 09/763,215, filed as application No. PCT/EP99/05682 on Aug. 6, 1999, now Pat. No. 6,469,054.

(30) Foreign Application Priority Data

Aug. 19, 1998 (DE) .......................... 198 37 638

(51) Int. Cl.$^7$ ...................... A61K 31/21; C07C 303/02; A61P 43/00
(52) U.S. Cl. ...................... 514/510; 514/517; 514/557; 514/708; 538/54
(58) Field of Search ................. 514/708, 510, 514/517, 557; 558/54

(56) References Cited

U.S. PATENT DOCUMENTS 5,532,237 A   7/1996   Gallant et al. ........... 514/235.2

FOREIGN PATENT DOCUMENTS

| EP | 19740785 | 8/1998 |
|----|----------|--------|
| JP | 58124758 | 7/1983 |
| WO | 9948871  | 9/1999 |

*Primary Examiner*—Joseph K. McKane
*Assistant Examiner*—Andrea D Small
(74) *Attorney, Agent, or Firm*—Susan M. Pellegrino

(57) ABSTRACT

The present invention relates to novel arylsulphonamides and analogues, to processes for their preparation and to their use for the prophylaxis and treatment of neurodegenerative disorders, in particular for the treatment of cerebral apoplexy, craniocerebral trauma, pain and spasticity.

23 Claims, No Drawings

ARYLSULPHONAMIDES AND ANALOGUES

This application is a continuing application of U.S. Ser. No. 09/763,215.

The present invention relates to novel arylsulphonamides and analogues, to processes for their preparation and to their use for the prophylaxis and treatment of neurodegenerative disorders, in particular for the treatment of cerebral apoplexy, craniocerebral trauma, pain and spasticity.

$\Delta^9$-Tetrahydrocannabinol ($\Delta^9$-THC) and, to a small extent, also $\Delta^8$-THC are the biologically active constituents in extracts of the plant Cannabis sativa (marihuana, hashish) and are responsible for the effects on the human central nervous system (CNS). Potential historical and contemporary therapeutic uses of cannabis preparations include, inter alia, analgesia, emesis, anorexia, glaucoma and mobility disorders.

Until now, two subtypes of cannabinoid receptors and a splice variant have been identified. The CB1 receptor (Nature 1990, 346, 561) and a splice variant CB1a (J. Biol. Chem. 1995, 270, 3726) are mainly localized in the central nervous system. The CB2 receptor was found mainly in peripheral tissue, in particular in leucocytes, spleen and macrophages (Eur. J. Biochem. 1995, 232, 54).

CB1 and CB2 receptors have seven transmembrane regions and belong to the family of G protein receptors. Both receptors are negatively coupled via $G_I/G_O$ protein to adenylate cyclase and possibly negatively coupled to the presynaptic release of glutamate (J. Neurosci. 1996, 16, 4322). CB1 receptors are moreover positively coupled to potassium channels and also negatively coupled to N- and Q-type calcium channels.

Four classes of CB1 receptor agonists are known to date: classical cannabinoids, such as, for example, $\Delta^9$-THC, non-classical cannabinoids, aminoalkylindoles and eicosanoids. The latter include the generally accepted endogenous CB1 receptor agonist anandamide.

It is additionally known that cerebral apoplexy is a consequence of a sudden circulatory disorder of a human brain region with subsequent functional losses, with corresponding neurological and/or psychological symptoms. The causes of cerebral apoplexy can lie in cerebral haemorrhages (e.g. after a vascular tear in hypertension, arteriosclerosis and appoplectic aneurysm) and ischaemias (e.g. due to a drop in blood pressure or embolism). The functional losses in the brain lead to a degeneration or destruction of brain cells (Journal of Cerebral Blood Flow and Metabolism 1981, 1, 155); Chem. Eng. News 1996 (May 13), 41; Trends Pharmacol. Sci. 1996, 17, 227). Craniocerebral trauma is understood as meaning covered and open cranial injuries with involvement of the brain.

The present invention relates to compounds of the general formula (I)

$$R^1\text{-}A\text{-}D\text{-}E\text{-}G\text{-}L\text{-}R^2 \quad (I)$$

in which $R^1$ represents a radical of the formula

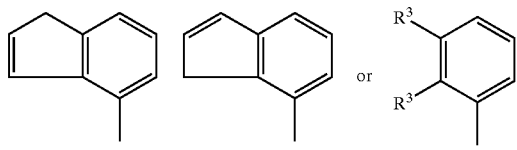

in which $R^3$ and $R^{3'}$ together with the phenyl double bond form a 5-membered, saturated, partially unsaturated or aromatic heterocycle which contains one or two heteroatoms from the group consisting of S, N and O or a radical of the formula —NQ,
in which
Q represents hydrogen or ($C_1$–$C_6$)-alkyl,
and where all of the ring systems listed above are optionally substituted, optionally geminally, by one or more identical or different substituents selected from the group consisting of:
halogen, carboxyl, hydroxyl, phenyl, ($C_1$–$C_6$)-alkoxy, ($C_1$–$C_6$)-alkoxycarbonyl, ($C_1$–$C_8$)-alkyl, which for its part may be substituted by halogen, $C_1$–$C_6$-alkylsulphonyloxy, azide, amino, mono($C_1$–$C_6$)-alkylamino, di($C_1$–$C_6$)-alkylamino or hydroxyl, a group of the formula —(CO)$_b$—NR$^4$R$^5$,
in which
b represents a number 0 or 1,
$R^4$ and $R^5$ are identical or different and independently of one another represent hydrogen, phenyl, ($C_1$–$C_6$)-acyl, cyclo($C_4$–$C_7$)-acyl benzoyl or ($C_1$–$C_6$)-alkyl, which is optionally substituted by amino, mono ($C_1$–$C_6$)-alkylamino, di($C_1$–$C_6$)-alkylamino,
or
$R^4$ and $R^5$ together with the nitrogen atom form a 5- or 6-membered saturated heterocycle which may optionally contain one or more further heteroatom(s) from the group consisting of S and O and/or one or more radical(s) of the formula —NR$^8$,
in which
$R^8$ represents hydrogen, ($C_1$–$C_6$)-alkyl or ($C_1$–$C_6$)-acyl,
and
a group of the formula —NR$^6$—SO$_2$—R$^7$
in which
$R^6$ represents hydrogen, phenyl, ($C_1$–$C_6$)-alkyl or ($C_1$–$C_6$)-acyl,
$R^7$ represents phenyl or ($C_1$–$C_6$)-alkyl,
and a radical of the formula

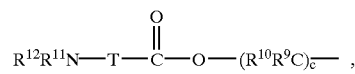

in which
c represents a number 1, 2, 3, 4, 5 or 6,
$R^9$ and $R^{10}$ are identical or different and represent hydrogen or ($C_1$–$C_6$)-alkyl,
T represents a radical of the formula —(CH$_2$)$_d$—,
in which
d represents a number 1, 2, 3, 4, 5 or 6,
or
T represents a moiety of an amino acid radical of the formula

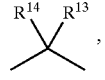

in which
$R^{13}$ and $R^{14}$ are identical or different and represent hydrogen or methyl,
or
$R^{13}$ represents hydrogen or methyl
and
$R^{14}$ represents ($C_3$–$C_8$)-cycloalkyl or ($C_6$–$C_{10}$)-aryl or hydrogen, or ($C_1$–$C_8$)-alkyl, where the $(C_1-C_8)$-alkyl is optionally substituted by methlythio, hydroxyl, mercapto, guanidyl or by a group of the formula $—NR^{15}R^{16}$ or $—NR^{17}—OC—$,
in which
$R^{15}$ and $R^{16}$ independently of one another represent hydrogen, $(C_1-C_8)$-alkyl or phenyl
and
$R^{17}$ represents hydroxyl, benzyloxy, $(C_1-C_8)$-alkoxy or the group $—NR^{15}R^{16}$ listed above,
or the $(C_1-C_8)$-alkyl is optionally substituted by (C3–C6)-cycloalkyl or phenyl, which for its part is substituted by hydroxyl, halogen or $(C_1-C_6)$-alkoxy or amino,
or the $(C_1-C_8)$-alkyl is optionally substituted by imidazolyl or indolyl, in which the corresponding —NH functions are optionally protected by $(C_1-C_6)$-alkyl or by an amino protective group,
$R^{11}$ and $R^{12}$ are identical or different and represent hydrogen, $(C_1-C_6)$-alkyl or a typical amino protective group,
or
$R^{11}$ and $R^{12}$ together with the nitrogen atom form a 5- to 6-membered saturated heterocycle, which may optionally contain a further heteroatom from the group consisting of S and O or a radical of the formula $—NR^{18}$,
in which
$R^{18}$ represents hydrogen, $(C_1-C_6)$-alkyl or phenyl,
A and E are identical or different and represent a bond or represent $(C_1-C_4)$-alkylene,
D represents an oxygen atom or represents a radical of the formula $—S(O)_e—$ or $—N(R^{19})—$,
in which
e represents a number 0, 1 or 2,
$R^9$ represents hydrogen, $(C_1-C_6)$-alkyl or $(C_1-C_6)$-acyl,
G represents doubly attached $(C_6-C_{10})$-aryl or represents a doubly attached 5- to 7-membered aromatic heterocycle having up to 3 heteroatoms from the group consisting of S, N and O which are optionally substituted by one or more identical or different substituents selected from the group consisting of:
hydroxyl, trifluoromethyl, carboxyl, halogen, $(C_1-C_6)$-alkyl, hydroxy$(C_1-C_6)$-alkyl, $(C_1-C_6)$-alkoxy, $(C_1-C_6)$-alkoxycarbonyl, and groups of the formulae $—CO—O—(CH_2)_f—NR^{20}R^{21}$, $—NR^{22}—SO_2R^{23}$, $—(CH_2)_g—(CO)_h—NR^{24}R^{25}$ and $—OR^{26}$,
in which
f represents a number 1, 2, 3 or 4,
g and h are identical or different and represent a number 0 or 1,
$R^{20}$ and $R^{21}$ have the meaning of $R^4$ and $R^5$ given above and are identical to or different from this meaning,
$R^{22}$ has the meaning of $R^6$ given above and is identical to or different from this meaning,
$R^{23}$ has the meaning of $R^7$ given above and is identical to or different from this meaning,
$R^{24}$ and $R^{25}$ have the meaning of $R^4$ and $R^5$ given above and are identical to or different from this meaning,
or independently of one another represent a radical of the formula $—(CH_2)_i—NR^{27}R^{28}$,
in which
i represents a number 1, 2, 3 or 4,
and
$R^{27}$ and $R^{28}$ have the meaning of $R^4$ and $R^5$ given above and are identical to or different from this meaning,
$R^{26}$ represents $(C_6-C_{10})$-aryl,
L represents a radical of the formula $—O—$, $—NH—$,

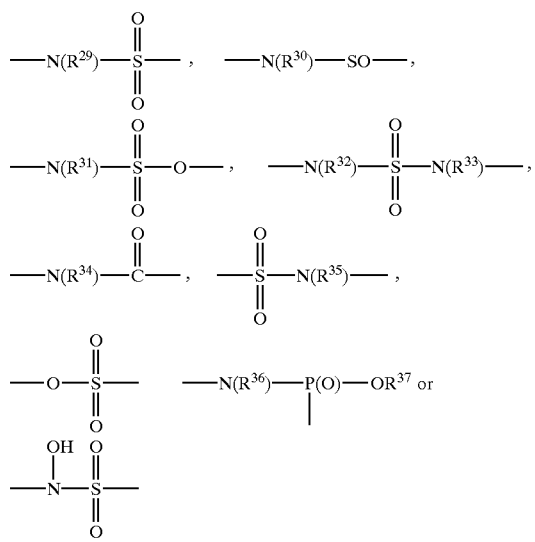

where the left-hand side of the radicals is attached to G, and in which $R^{29}$, $R^{30}$, $R^{31}$, $R^{32}$, $R^{33}$, $R^{34}$, $R^{35}$, $R^{36}$ and $R^{37}$ are identical or different and represent hydrogen or $(C_1-C_4)$-alkyl,
or
$R^{29}$ represents a radical of the formula $—SO_2R^2$,
$R^2$ represents $(C_6-C_{10})$-aryl or represents a 5- to 7-membered saturated or aromatic heterocycle having up to 3 heteroatoms from the group consisting of S, N and O, which are optionally substituted by one or more identical or different substituents selected from the group consisting of:
halogen, trifluoromethyl, nitro, amino and $(C_1-C_6)$-alkyl,
or
represents the radical of the formula

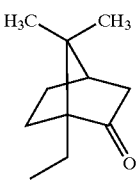

or morpholine, or represents $C_3-C_8$-cycloalkyl, or represents $(C_1-C_{12})$-alkyl, $(C_2-C_{12})$-alkenyl or $(C_2-C_{12})$-alkinyl, which are optionally substituted by one or more identical or different substituents selected from the group consisting of:
halogen, trifluoromethyl, hydroxyl, cyano, azido, $(C_1-C_6)$-alkoxy, $(C_1-C_6)$-perfluoroalkoxy, partially fluorinated $(C_1-C_6)$-alkoxy, a radical of the formula

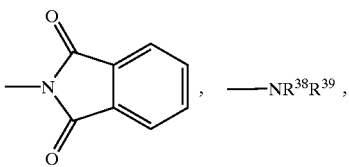, —NR³⁸R³⁹, in which
R³⁸ and R³⁹ have the meaning of R⁴ and R⁵ given above and are identical to or different from this meaning,
phenyl, optionally substituted by one or more identical or different substituents selected from the group consisting of:
halogen, nitro, hydroxyl, $(C_1-C_6)$-alkyl, $(C_1-C_6)$-alkoxy and a group of the formula —NR⁴⁰R⁴¹,
in which
R⁴⁰ and R⁴¹ are identical or different and represent hydrogen or $(C_1-C_6)$-alkyl or $(C_1-C_6)$-acyl,
and a 5- to 6-membered aromatic heterocycle having up to three heteroatoms from the group consisting of S, N and O optionally substituted by one or more identical or different substituents selected from the group consisting of:
halogen, nitro, hydroxyl, $(C_1-C_6)$-alkyl, $(C_1-C_6)$-alkoxy and a group of the formula —NR⁴⁰R⁴¹,
in which
R⁴⁰ and R⁴¹ are as defined above,
or
L and R² together represent a radical of the formula

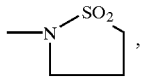, and pharmaceutically acceptable salts thereof,
with the proviso that R¹ does not represent an unsubstituted radical or a substituted radical of the formula

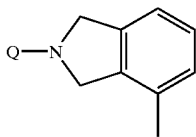

as defined above, in which Q is as defined above.

In the context of the invention, amino protective group are the customary amino protective groups used in peptide chemistry. These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichloroethoxycarbonyl, 2,2,2-trichloro-tert-butoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl or 4-nitrophenyl.

The compounds according to the invention can exist in stereoisomeric forms which are either like image and mirror image (enantiomers) or which are not like image and mirror image (diastereomers). The invention relates both to the enantiomers or diastereomers and to their respective mixtures. These mixtures of the enantiomers and diastereomers can be separated in a known manner into the stereoisomerically uniform components.

The compounds according to the invention can also be present in the form of their salts. In general, salts with organic or inorganic bases or acids may be mentioned here.

In the context of the present invention, preference is given to physiologically acceptable salts. Physiologically acceptable salts of the compounds according to the invention can be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention. Particular preference is, for example, given to sodium, potassium, magnesium or calcium salts, and to ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The present invention also includes ammonium compounds which can be prepared by converting the free amines by alkylation.

In the context of the present invention, the substituents generally have the following meaning:

$(C_1-C_{12})$-Alkyl generally represents, depending on the abovementioned substituents, a straight-chain or branched hydrocarbon radical having 1 to 12 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl. Preference is given to $(C_1-C_8)$-alkyl having 1 to 8 carbon atoms, for example methyl, ethyl, propyl, isopropyl.

$(C_1-C_{12})$-Alkenyl generally represent, depending on the abovementioned substituents, a straight-chain or branched hydrocarbon radical having 2 to 6 and 2 to 20 carbon atoms and one or more, preferably one or two, double bonds. Preference is given to the lower alkyl radical having 2 to 4 and 2 to 10 carbon atoms and one double bond. Particular preference is given to an alkenyl radical having 2 to 3 and 2 to 8 carbon atoms and one double bond. Examples which may be mentioned are allyl, propenyl, isopropenyl, butenyl, isobutenyl, pentenyl, isopentenyl, hexenyl, isohexenyl, heptenyl, isoheptenyl, octenyl and isooctenyl.

$(C_2-C_{12})$-Alkinyl generally represents, depending on the abovementioned substituents, a straight-chain or branched hydrocarbon radical having 2 to 12 carbon atoms and one or more, preferably one or two, triple bonds. Preference is given to the lower alkyl radical having 2 to about 10 carbon atoms and one triple bond. Particular preference is given to an alkyl radical having 2 to 8 carbon atoms and one triple bond. Examples which may be mentioned are acetylene, 2-butine, 2-pentine and 2-hexine.

$(C_1-C_6)$-Acyl generally represents, depending on the abovementioned substituents, straight-chain or branched lower alkyl having 1 to 6 carbon atoms, which are attached via a carbonyl group. Particular preference is given to alkyl radicals having up to 4 carbon atoms. Very particular preference is, for example, given to alkyl radicals having up to 3 carbon atoms. Examples which may be mentioned are: acetyl, ethylcarbonyl, propylcarbonyl, isopropylcarbonyl, butylcarbonyl and isobutylcarbonyl.

$(C_1-C_6)$-Alkoxy generally represents, depending on the abovementioned substituents, a straight-chain or branched hydrocarbon radical having 1 to 6 carbon atoms, which is attached via an oxygen atom. Preference is given to lower alkoxy having 1 to 4 carbon atoms. Particular preference is given to an alkoxy radical having 1 to 3 carbon atoms. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

$(C_1-C_6)$-Alkoxycarbonyl can be represented, for example, by the formula

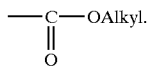

Here, alkyl represents a straight-chain or branched hydrocarbon radical having 1 to 6 carbon atoms. Preference is given to lower alkoxycabonyl having 1 to 4 carbon atoms in the alkyl moiety. The following alkoxycarbonyl radicals may be mentioned by way of example: methoxycarbonyl, ethoxycarbonyl, propoxycarbonyl, isopropoxycarbonyl, butoxycarbonyl or isobutoxycarbonyl.

$(C_3-C_8)$-Cycloalkyl generally represents a cyclic hydrocarbon radical having 3 to 8 carbon atoms. Preference is given to cyclopropyl, cyclopentyl and cyclohexyl. Examples which may be mentioned are cyclopentyl, cyclohexyl, cycloheptyl and cyclooctyl.

cyclo$(C_4-C_7)$-Acyl generally represents, depending on the abovementioned substituents, cyclopropylcarbonyl, cyclobutylcarbonyl, cyclopentylcarbonyl or cyclohexylcarbonyl.

$(C_6-C_{10})$-Aryl generally represents an aromatic radical having 6 to 10 carbon atoms. Preferred aryl radicals are phenyl and naphthyl.

$(C_1-C_6)$-Perfluoroalkoxy in the context of the invention represents an alkoxy radical having 1 to 6 carbon atoms and 3 to 13 fluorine atoms. Preference is given to an alkoxy radical having 1 to 5 carbon atoms and 3 to 9 fluorine atoms.

$(C_1-C_6)$-Partially fluorinated alkoxy in the context of the invention represents an alkoxy radical having 1 to 6 carbon atoms and 3 to 5 fluorine atoms. Preference is given to an alkoxy radical having 1 to 4 carbon atoms and 3 fluorine atoms. Particular preference is given to an alkoxy radical having 1 to 3 carbon atoms and which is substituted by trifluoromethyl.

Halogen in the context of the invention represents fluorine, chlorine, bromine and iodine.

Aromatic, saturated and unsaturated heterocycles in the context of the invention, depending on the abovementioned substituents, in general represent a 5- to 7-membered or 5- to 6-membered, preferably 5- to 6-membered, heterocycle which may contain up to 3 heteroatoms from the group consisting of S, N and O and which may optionally also be attached via a nitrogen atom. Examples which may be mentioned are: pyridyl, thienyl, furyl, pyrrolyl, pyrrolidinyl, piperazinyl, pyrimidyl, thiazolyl, oxazolyl, imidazolyl, morpholine or piperidyl. Preference is given to pyridyl, furyl, morpholine, piperidyl and piperazinyl.

$(C_3-C_6)$-Ketone in the context of the invention represents a saturated or unsaturated ketone having 3 to 6 carbon atoms. Examples which may be mentioned are: acetone, butanone, but-1-en-3-one, but-1-in-3-one, pentan-3-one, pentan-2-one, pent-1-en-3-one, pent-1-in-3-one, penta-1,4-dien-3-one, 3-methylbutan-2-one, cyclopropyl methyl ketone, cyclopentanone, hexan-2-one, hexan-3-one, cyclohexanone, 2-methylcyclopentanone, 2-ethylcyclobutanone.

$(C_1-C_6)$-Aldehyde in the context of the invention represents a saturated or unsaturated aldehyde having 1 to 6 carbon atoms. Examples which may be mentioned are: formaldehyde, acetaldehyde, propionaldehyde, butyraldehyde, isobutyraldehyde, cyclopropylcarbaldehyde, but-2-enal, but-2-inal, pentanal, isopentanal, pivaldehyde, cyclobutylcarbaldehyde, 2-methylcyclopropylcarbaldehyde, pent-2-enal, pent-4-enal, hexanal, 2-cyclobutylacetaldehyde.

Preference is given to compounds of the formula (I), in which $R^1$ represents a radical of the formula

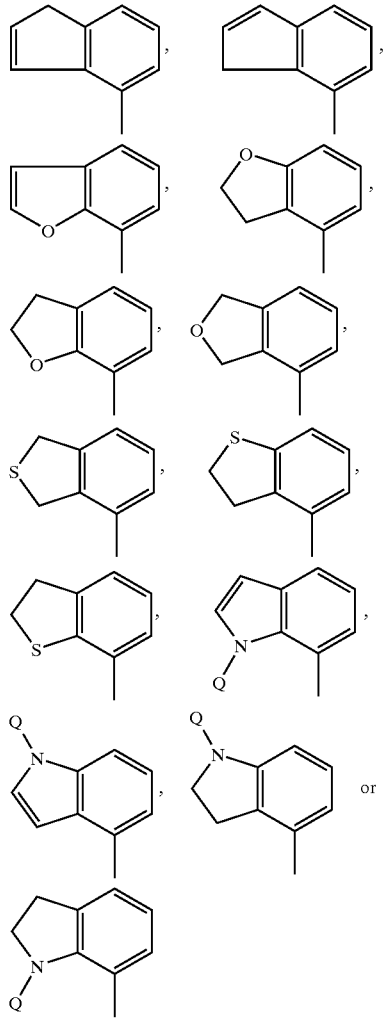

in which

Q represents hydrogen or $(C_1-C_3)$-alkyl, and where the ring systems listed above are optionally substituted, optionally geminally, by one or more identical or different substituents selected from the group consisting of:

fluorine, chlorine, carboxyl, hydroxyl, $(C_1-C_4)$-alkoxy, $(C_1-C_5)$-alkoxycarbonyl or $(C_1-C_6)$-alkyl, which for its part may be substituted by fluorine, chlorine or hydroxyl, and a radical of the formula

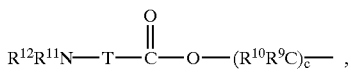

in which c represents a number 1, 2, 3, 4, 5 or 6, $R^9$ and $R^{10}$ are identical or different and represent hydrogen or $(C_1-C_6)$-alkyl, T represents a radical of the formula $-(CH_2)_d-$, in which d represents a number 1, 2, 3, 4, 5 or 6, or T represents a moiety of an amino acid radical of the formula

in which $R^{13}$ and $R^{14}$ are identical or different and represent hydrogen or $(C_1-C_6)$-alkyl, or $R^{13}$ represents hydrogen or methyl and $R^{14}$ represents cyclopropyl, cyclopentyl, cyclohexyl, phenyl or hydrogen, or represents $(C_1-C_6)$-alkyl, where the alkyl is optionally substituted by methylthio, hydroxyl, mercapto, guanidyl or by a group of the formula $-NR^{15}R^{16}$ or $-NR^{17}-OC-$, in which $R^{15}$ and $R^{16}$ independently of one another represent hydrogen, $(C_1-C_8)$-alkyl or phenyl and $R^{17}$ represents hydroxyl, benzyloxy, $(C_1-C_6)$-alkoxy or the group $-NR^{15}R^{16}$ listed above, or the $(C_1-C_6)$-alkyl is optionally substituted by cyclopropyl, cyclopentyl, cyclohexyl or phenyl, which for its part is substituted by hydroxyl, fluorine, chlorine, bromine or $(C_1-C_4)$-alkoxy or amino, or $R^{11}$ and $R^{12}$ are identical or different and represent hydrogen or $(C_1-C_4)$-alkyl, or $R^{11}$ and $R^{12}$ together with the nitrogen atom form a morpholinyl piperidinyl or piperazinyl ring, A and E are identical or different and represent a bond or represent $(C_1-C_4)$-alkylene, D represents an oxygen atom, G represents doubly attached phenyl or pyridyl, which are optionally substituted by one or more identical or different substituents selected from the group consisting of:

hydroxyl, trifluoromethyl, carboxyl, halogen, $(C_1-C_4)$-alkyl, hydroxy$(C_1-C_4)$-alkyl, $(C_1-C_4)$-alkoxy, $(C_1-C_4)$-alkoxycarbonyl, and groups of the formulae $-CO-O-(CH_2)_f-NR^{20}R^{21}$, $-NR^{22}-SO_2R^{23}$, $-(CH_2)_g(CO)_h-NR^{24}R^{25}$ and $-OR^{26}$, in which f represents a number 1, 2, 3 or 4, g and h are identical or different and represent a number 0 or 1, $R^{20}$ and $R^{21}$ have the meaning of $R^4$ and $R^5$ given above and are identical to or different from this meaning, $R^{22}$ has the meaning of $R^6$ given above and is identical to or different from this meaning, $R^{23}$ has the meaning of $R^7$ given above and is identical to or different from this meaning, $R^{24}$ and $R^{25}$ have the meaning of $R^4$ and $R^5$ given above and are identical to or different from this meaning, or independently of one another represent a radical of the formula $-(CH_2)_i-NR^{27}R^{28}$, in which i represents a number 1, 2 or 3, and $R^{27}$ and $R^{28}$ have the meaning of $R^{20}$ and $R^{21}$ given above and are identical to or different from this meaning, $R^{26}$ represents phenyl or naphthyl, L represents a radical of the formula

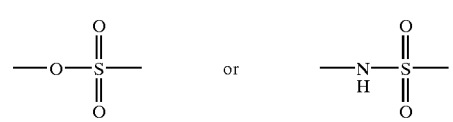

where the left-hand side of the radicals is attached to G, $R^2$ represents $(C_1C_{10})$-alkyl, which is optionally substituted by one or more identical or different substituents selected from the group consisting of:

fluorine, chlorine, bromine, phenyl, trifluoromethyl, hydroxyl, azido, $(C_1-C_4)$-alkoxy, $(C_1-C_5)$-perfluoroalkoxy or partially fluorinated $(C_1-C_4)$ alkoxy and pharmaceutically acceptable salts thereof.

Particular preference is given to compounds of the formula (I), in which $R^1$ represents a radical of the formula

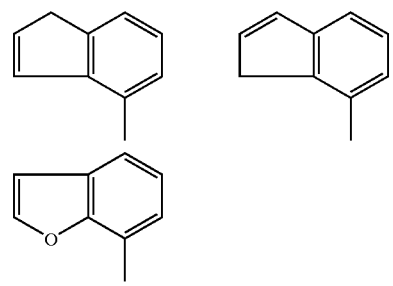

and where the ring systems listed above are optionally substituted by one or more identical or different substituents selected from the group consisting of:

chlorine, fluorine, hydroxyl, $(C_1-C_3)$-alkoxy or $(C_1-C_4)$-alkyl, which for its part may be substituted by hydroxyl, A and E are identical or different and represent a bond, D represents an oxygen atom, G represents doubly attached phenyl, which is optionally substituted by one or more identical or different substituents selected from the group consisting of:
hydroxyl, trifluoromethyl, carboxyl, fluorine, chlorine, bromine, $(C_1-C_3)$-alkyl, hydroxy$(C_1-C_3)$alkyl or $(C_1-C_3)$-alkoxy L represents a radical of the formula

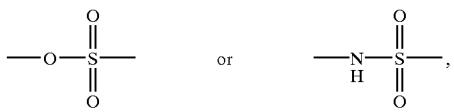

where the left-hand side of the radicals is attached to G, $R^2$ represents $(C_1-C_8)$-alkyl which is optionally substituted by one or more identical or different substituents selected from the group consisting of:
fluorine, chlorine, bromine, phenyl, trifluoromethyl, or trifluoromethyl-substituted $(C_1-C_4)$-alkoxy and pharmaceutically acceptable salts thereof.

Very particular preference is given to compounds of the formula (I), in which $R^1$ represents a radical of the formula

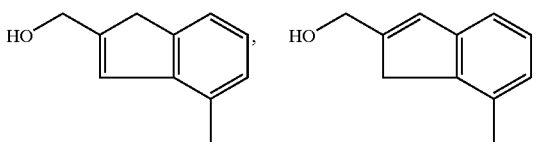

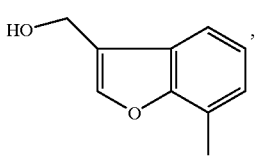

A and E represent a bond,

D represents an oxygen atom,

G represents doubly attached phenyl which is optionally substituted by fluorine, chlorine or bromine, L represents a radical of the formula

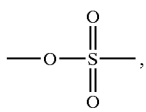

where the left-hand side of the radical is attached to G, $R^2$ represents $(C_1-C_4)$-alkyl, which is optionally substituted by fluorine or trifluoromethyl and pharmaceutically acceptable salts thereof.

Very particular preference is given to compounds selected from the group consisting of

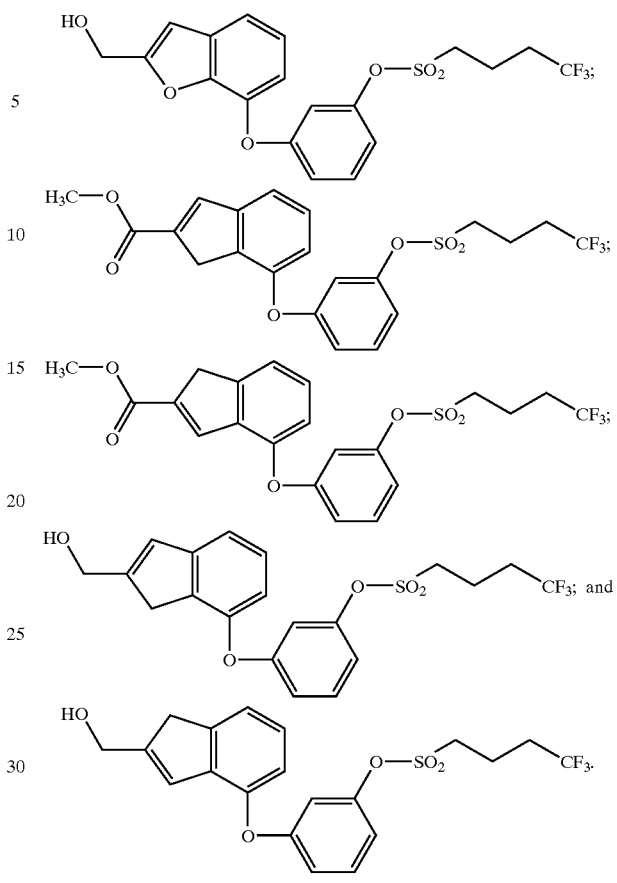

Moreover, we have found a process for preparing the compounds of the general formula (I) according to the invention, characterized in that compounds of the general formula (II)

[A] compounds of the general formula (IV)

$$R^1\text{-A-D-E-G-M-H} \qquad (II)$$

in which $R^1$, A, D, E and G have the meaning given above and

M represents oxygen or —N($R^{42}$)—, in which $R^{42}$ represents hydrogen or $(C_1-C_4)$-alkyl, are reacted with compounds of the general formula (III)

$$R^{43}\text{—U—}R^2 \qquad (III)$$

in which $R^2$ has the meaning given in claim 1, $R^{43}$ represents halogen, preferably chlorine or iodine, U represents a radical of the formula —$SO_2$—, —SO—, —CO—, —P(O)(O$R^{37}$)— or a single bond, in which $R^{37}$ has the meaning given above, to give compounds of the general formula (Ia)

$$R^1\text{-A-D-E-G-M-U—}R^2 \qquad (Ia)$$

in which $R^1$, A, D, E, G, M, U and $R^2$ have the meaning given above, in inert solvents, if appropriate in the presence of a base,
or

[B] compounds of the general formula (II)
are initially reacted with trialkylsilyl chlorosulphonates, preferably trimethylsilyl chlorosulphonate, admixed with an acid and then reacted with a chlorinating agent, preferably phosphorus pentachloride, to give a compound of the general formula (IV)

$$R^{1''}\text{-A-D-E-G-M-SO}_2\text{—Cl} \qquad (IV)$$

in which $R^1$, A, D, E, G and M have the meaning given above, followed by reaction with compounds of the general formula (V)

$$H\text{—V—}R^2 \qquad (V)$$

in which $R^2$ has the meaning given in claim 1 and

V represents oxygen or nitrogen, to give compounds of the general formula (Ib)

$$R^1\text{-A-D-E-G-M-SO}_2\text{—V—}R^2 \qquad (Ib)$$

in which $R^1$, A, D, E, G, M, V and $R^2$ have the meaning given above, in inert solvents in the presence of $Bzl\text{-NEt}_3{}^+Cl^-$ and a base, or

[C] compounds of the general formula (VI)

$$R^1\text{-A-D'-H} \qquad (VI)$$

in which $R^1$ and A have the meaning given above and

D' represents oxygen, sulphur or —N($R^{19}$)— and $R^{19}$ has the meaning given above, are reacted with compounds of the general formula (VII)

$$R^{44}\text{-E-G-SO}_2\text{—NH—}R^2 \qquad (VII)$$

in which

E, G and $R^2$ have the meaning given above and $R^{44}$ represents a leaving group, preferably halogen, particularly preferably fluorine, chlorine or bromine, to give compounds of the general formula (Ic)

$$R^1\text{-A-D'-E-G-SO}_2\text{—NH—}R^2 \qquad (Ic)$$

in which $R^1$, A, D', E, G and $R^2$ have the meaning given above, or

[D] compounds of the general formula (Id)

$$R^{45}\text{-A-D-E-G-L-}R^2 \qquad (Id)$$

in which

A, D, E, G, L and $R^2$ have the meaning given above and $R^{45}$ represents radicals of the formulae

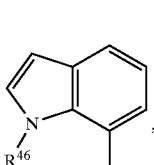, 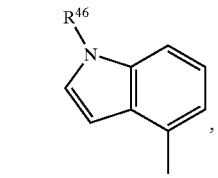,

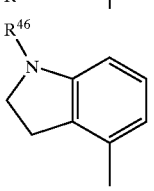 or 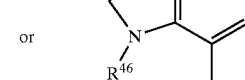

in which $R^{46}$ represents $(C_1\text{-}C_6)$-alkyl, are reacted with chloroformate, preferably 1-(1-chloro)ethyl chloroformate or methyl chloroformate, and then with alcohols, preferably methanol, if appropriate in the presence of a base, to give compounds of the general formula (Ie)

$$R^{47}\text{-A-D-E-G-L-}R^2 \qquad (Ie)$$

in which

A, D, E, G, L and $R^2$ have the meaning given above and $R^{47}$ represents radicals of the formulae

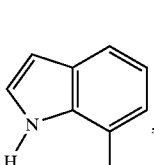, 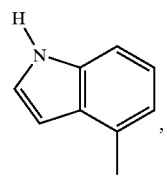,

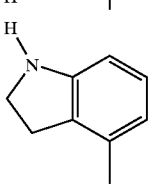 or 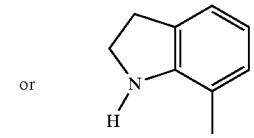

or

[E] compounds of the general formula (Ie)
are reacted with $(C_1\text{-}C_6)$-ketones or $(C_1\text{-}C_6)$-aldehydes in the presence of a reducing agent, preferably sodium cyanoborohydride, if appropriate in the presence of an acid, to give compounds of the general formula (If)

$$R^{48}\text{-A-D-E-G-L-}R^2 \qquad (If)$$

in which

A, D, E, G, L and $R^2$ have the meaning given above and $R^{48}$ represents $(C_3\text{-}C_6)$-alkenyl or $(C_1\text{-}C_6)$-alkyl, or

[F] compounds of the general formula (Ie) [lacuna] with compounds of the general formula (VIII)

$$R^{49}\text{—Q} \qquad (VIII)$$

in which

Q has the meaning given above, $R^{49}$ represents a leaving group, preferably halogen, in inert solvents, if appropriate in the presence of a base, to give compounds of the general formula (Ig)

$R^{50}$-A-D-E-G-L-$R^2$ (Ig)

in which
A, D, E, G, L and $R^2$ have the meaning given above and
$R^{50}$ represents a radical of the formula

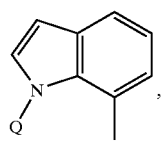 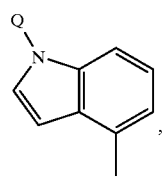

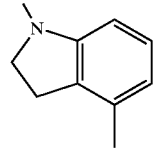 or 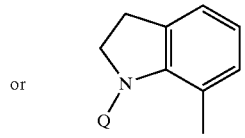

in which
Q has the meaning given above,
or
[G] compounds of the general formula (Ih)

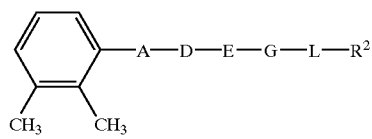 (Ih)

in which
A, D, E, G, L and $R^2$ have the meaning given above,
are converted by free-radical bromination, for example using N-bromosuccinimide, in an inert solvent into compounds of the general formula (Ii)

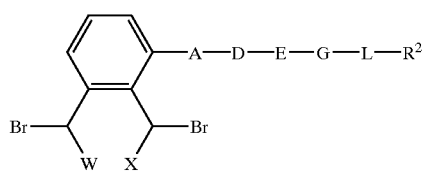 (Ii)

in which
A, D, E, G, L and $R^2$ have the meaning given above,
and one of the substituents W or X represents bromine and the other represents hydrogen,
and subsequently reacted with compounds of the general formula (IX)

CH$_2$(CO$_2$R$^{51}$)$_2$ (IX)

in which
$R^{51}$ represents (C$_1$–C$_6$)-alkyl and
in inert solvents, if appropriate in the presence of a base, to give compounds of the general formula (Ij)

$R^{52}$-A-D-E-G-L-$R^2$ (Ij)

in which
A, D, E, G, L and $R^2$ have the meaning given above and $R^{52}$ represents a radical of the formula

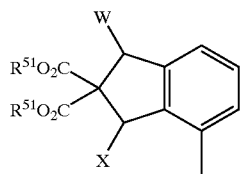

in which
$R^{51}$, W and X have the meaning given above,
to give compounds of the general formula (X)

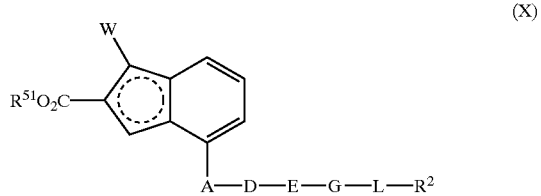 (X)

in which
A, D, E, G, L, $R^2$, W and $R^{51}$ have the meaning given above,
and finally reduced to the methylhydroxy function,
or
[H] in the case that $R^1$ represents the rings listed above, which are substituted by the radical of the formula $R^{12}R^{11}N$—T—$\overset{\overset{O}{\|}}{C}$—O—(R$^{10}$R$^9$C)$_{\overline{c}}$— in which
c, T, $R^9$, $R^{10}$, $R^{11}$ and $R^{12}$ have the meaning given above,
compounds of the general formula (XI)

$R^1$—(CR$^9$R$^{10}$)$_c$—OH (XI)

are reacted with compounds of the general formula (XII)

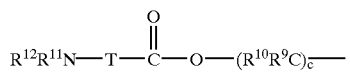 (XII)

in which
T has the meaning given above,
$R^{11'}$ represents hydrogen
and
$R^{12'}$ represents one of the amino protective groups listed above, preferably tert-butyloxycarbonyl,
in inert solvents, if appropriate in the presence of a base and an auxiliary,
and the amino protective group is cleaved off by customary methods,
and, if appropriate, the amino group is then dialkylated or alkylated reductively with an aldehyde or ketone,
or alkylated or dialkylated with a halide,
followed, if appropriate and depending on the substituents listed above, by derivatization by customary methods such as, for example, an alkylation or esterification, and, in a last step, a reduction with $BH_3 \times S(CH_3)_2$ in tetrahydrofuran is carried out, and, in the case of the pure enantiomers, an HPLC separation is carried out by customary methods, and, if appropriate, the substituents listed above are introduced by customary methods and derivatized, and, in the case that D=—SO— or —SO$_2$—, an oxidation is carried out on the corresponding thioethers (D=S) by customary methods, and, in the case of the ammonium compounds, an alkylation is carried out on the corresponding amines.

The processes according to the invention can be illustrated in an exemplary manner by the formula schemes below:

[A]

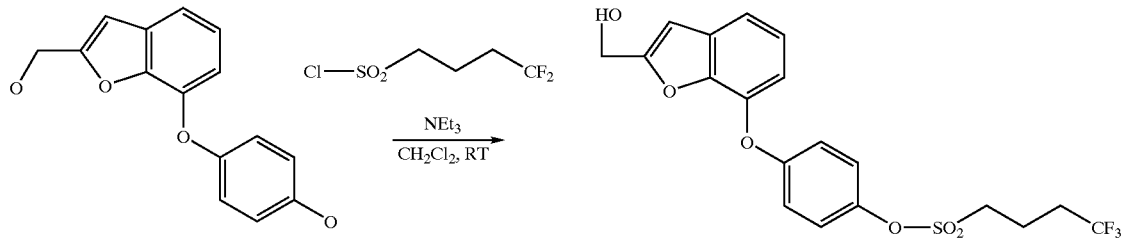

[B]

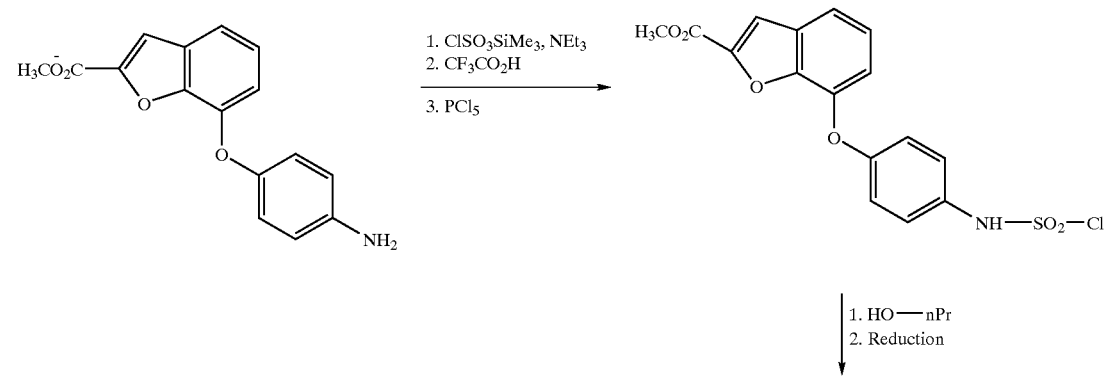

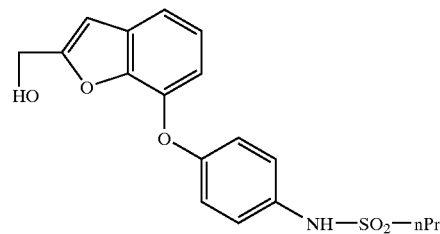

[C]

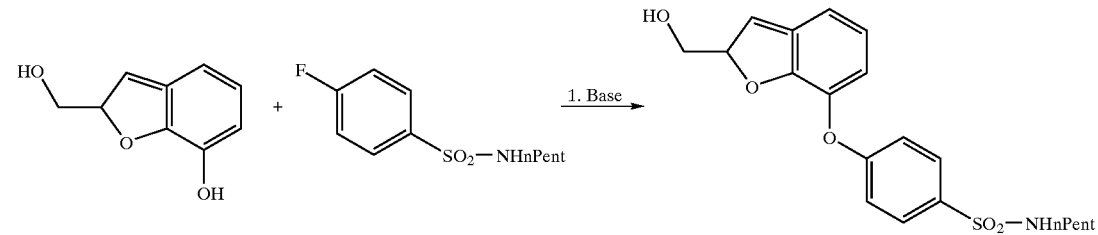

[D]

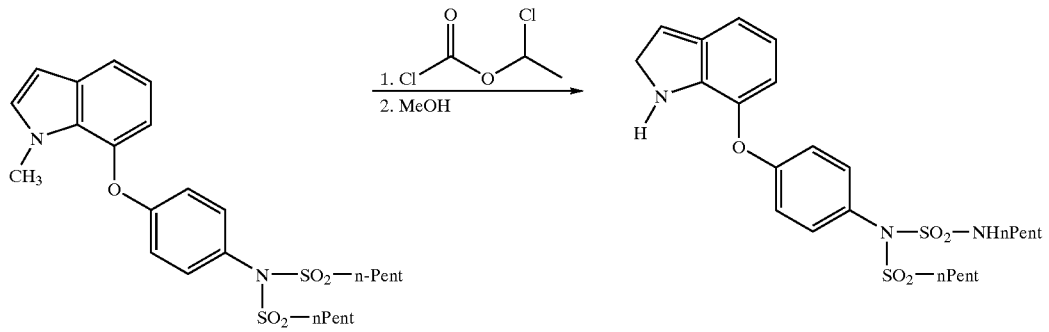

[E]

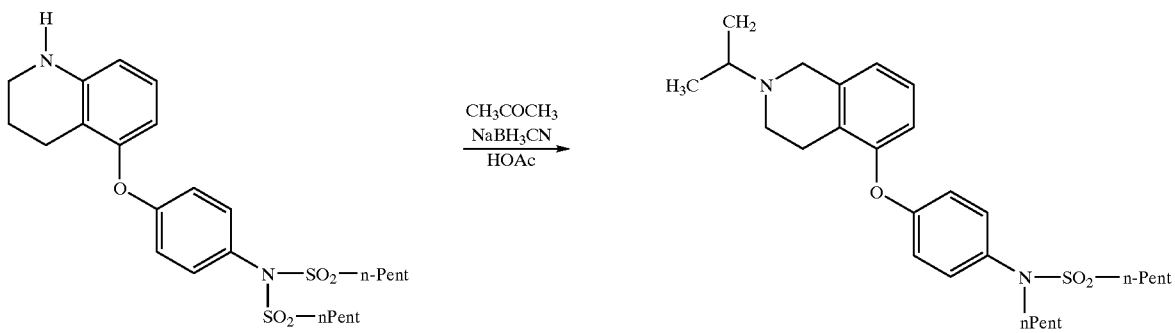

[G]

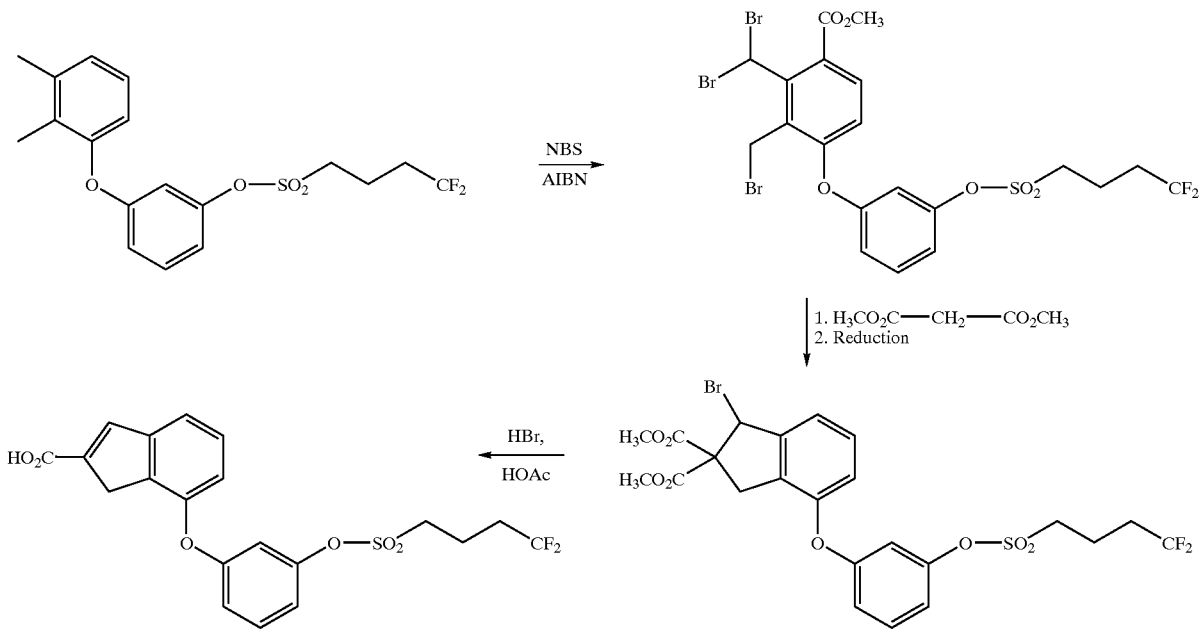

Suitable solvents are ethers, such as diethyl ether, dioxane, tetrahydrofuran, glycol dimethyl ether, or hydrocarbons, such as benzene, toluene, xylene, hexane, cylcohexane or mineral oil fractions, or halogenated hydrocarbons, such as dichloromethane, trichloromethane, carbon tetrachloride, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to use mixtures of the solvents mentioned. Dichloromethane is preferred.

In general, suitable bases are alkali metal hydrides or alkoxides, such as, for example, sodium hydride or potassium tert-butoxide, or cyclic amines, such as, for example, piperidine, pyridine, dimethylaminopyridine, or $C_1$–$C_4$-alkylamines, such as, for example, triethylamine. Triethylamine, sodium hydride, pyridine and/or dimethylaminopyridine are preferred.

Suitable bases are additionally the customary inorganic bases. These preferably include alkali metal hydroxides or alkaline earth metal hydroxides, such as, for example, sodium hydroxide, potassium hydroxide or barium hydroxide, or alkali metal carbonates, such as sodium carbonate or potassium carbonate, or sodium bicarbonate, or alkali metal alkoxides, such as sodium methoxide, sodium ethoxide, potassium methoxide, potassium ethoxide or potassium tert-butoxide. Potassium carbonate and sodium hydroxide are particularly preferred.

In one variant, the reaction is carried out in pyridine to which a catalytic amount of DMAP has been added. If appropriate, it is also possible to add toluene.

The processes are generally carried out at atmospheric pressure. However, it is also possible to carry out the processes under elevated pressure or under reduced pressure (for example in a range of from 0.5 to 5 bar).

The compounds of the general formula (II) can, for example, be prepared by

[A'] reacting compounds of the general formula (XIII)

  (XIII)

in which $R^1$, A and D' have the meaning given above with compounds of the general formula (XIV)

  (XIV)

in which

E and G have the meaning given above and $R^{53}$ represents a leaving group, preferably halogen, in inert solvents, if appropriate in the presence of a base, and then with customary reducing agents, preferably $H_2$/Pd/C in an inert solvent or with hydrazine hydrate, Pd/C, if appropriate with simultaneous hydrogenation of (C—C) multiple bonds, to give compounds of the general formula (IIa)

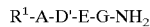  (IIa)

in which $R^1$, A, D', E and G have the meaning given above, or

[B'] reacting compounds of the general formula (IIb)

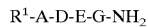  (IIb)

in which $R^1$, A, D, E and G have the meaning given in claim 1, with a nitrosating agent, preferably an aqueous solution of sulphuric acid and sodium nitrite and subsequent heating, preferably to 60 to 100° C., to give compounds of the general formula (IIc)

  (IIc)

in which $R^1$, A, D, E and G have the meaning given above, or

[C'] reacting compounds of the general formula (XV)

  (XV)

in which $R^1$ has the meaning given above and $R^{54}$ represents a leaving group, preferably halogen, particularly preferably bromine, with compounds of the general formula (XVI)

  (XVI)

in which

G has the meaning given above and $R^{55}$ represents $(C_1-C_6)$-alkyl, preferably methyl, in an inert solvent, preferably dimethylformamide or pyridine, if appropriate in the presence of a base, preferably potassium carbonate, and if appropriate in the presence of copper (I/II) salts, preferably copper (II) oxide or copper (I) iodide, in a temperature range of from 0° C. to 200° C., preferably from 80 to 150° C. and at atmospheric pressure to give compounds of the general formula (Ik)

  (Ik)

in which $R^1$, G and $R^{55}$ have the meaning given above, and then in the presence of an acid, preferably hydrobromic acid, to give compounds of the general formula (IId)

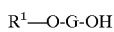  (IId)

or

[D'] compounds of the general formula (XVII)

  (XVII)

in which $R^1$ A and D' have the meaning given above, are reacted with compounds of the general formula (XVIII)

  (XVIII)

in which $R^{56}$ has the meaning given for $R^{55}$ and is identical to or different from this meaning, E has the meaning mentioned above, G' represents a doubly attached 5- to 7-membered aromatic heterocycle having up to 3 heteroatoms from the group consisting of sulphur, nitrogen and oxygen, which may optionally be substituted by one or more, identical, or different substituents as described above for G and $R^{57}$ represents halogen, preferably chlorine or bromine, to give a compound of the general formula (XIX)

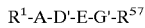  (XIX)

in which $R^1$, A, D', E, G' and $R^{57}$ have the meaning mentioned above, in inert solvents, if appropriate in the presence of a base, and then transformed with potassium amide in liquid ammonia into the corresponding free amines of the general formula (IIe)

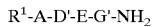  (IIe)

in which

R¹, A, D', E and G' have the meaning given above.

DOS (German Published Specification) 1 942 264 describes the preparation of fluorinated alkanesulphonyl chlorides, U.S. Pat. No. 5,149,357 describes, inter alia, the preparation of a 4,4,4-trifluorobutanesulphonamide, but without disclosing the preparation of the corresponding sulphonyl chloride.

The fluorinated sulphonyl chlorides were prepared analogously to DOS (German Published Specification) 1 942 264.

The compounds of the general formulae (III), (V), (VI), (VII), (VIII), (IX), (X), (XI) and (XII) are known per se or can be prepared by customary methods.

The compounds of the general formulae (Ia), (Ib), (Ic), (Id), (Ie), (If), (Ig), (Ii), (Ij), (IIa), (IIb), (IIc), (IId), (IIe), (IIf), (III), (IV), (XIV), (XVI) (XVII) and (XVIII) are novel and can be prepared as described above.

The alkylation to prepare the ammonium compounds is generally carried out using alkylating agents, such as, for example, alkyl halides, sulphonic acid esters or substituted or unsubstituted dialkyl or diaryl sulphonates, preferably using methyl iodide or dimethyl sulphate.

The alkylation is generally carried out in one of the abovementioned solvents, preferably in dimethylformamide, in a temperature range of from 0° C. to +70° C., preferably from 0° C. to +30° C. and atmospheric pressure.

Some of the compounds of the general formula (IIh) are known, or they are novel and can be [lacuna] by reacting the compounds of the general formulae (XX) and (XXI)

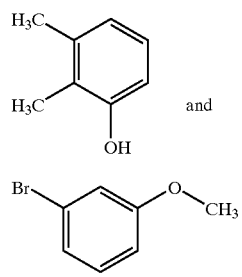

(XX)

and

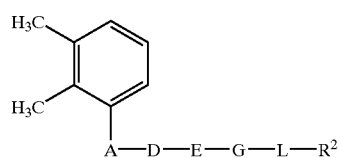

(XXI)

in the presence of CuO (cat), potassium carbonate and pyridine, to give the compounds of the general formula (XXII)

(XXII)

H₃C\
H₃C⧸⟨⟩—A—D—E—G—L—R² in which
A, D, E, G, L and R² have the meaning given above, and then liberating the hydroxyl function using hydrobromic acid and glacial acetic acid.

The compounds of the general formulae (XX) and (XXI) are known per se or can be prepared by customary methods.

The compounds of the general formula (XXII) can be prepared as described above.

Preference is given to compounds of the general formula (I) whose solubility in 0.9% strength aqueous sodium chloride solution at 25° C. is above 10 mg/l, particularly preferably above 100 mg/l.

Surprisingly, the novel aryl sulphonamides and their analogues show an unforeseeable, useful spectrum of pharmacological action.

They are distinguished as highly effective agonists of the CB1 receptor and in some cases of the CB2 receptor. They can be employed alone or in combination with other medicaments for the treatment and/or prevention of neuronal damage of varying cause, such as, for example, due to ischaemic, thrombic and/or thromboembolic, and haemorrhagic stroke, and conditions after direct and indirect injuries in the area of the brain and of the skull; furthermore for the treatment and/or prevention of cerebral ischaemias after all operative interventions in the brain or peripheral organs or body parts and conditions of pathogenic or allergic nature accompanying or preceding them, which can lead primarily and/or secondarily to neuronal damage. Likewise, the compounds according to the invention are also suitable for the therapy of primary and/or secondary pathogenic conditions of the brain, for example during or after cerebral vasospasms, migraine, spasticity hypoxia and/or anoxia of previously unmentioned origin, perinatal asphyxia, autoimmune disorders, metabolic and organ disorders which can be accompanied by damage to the brain and also damage to the brain as a result of primary brain disorders, for example convulsive conditions and athero- and/or arteriosclerotic changes; for the treatment of chronic or psychiatric conditions such as, for example, depression, neurodegenerative disorders such as, for example, Alzheimer's, Parkinson's or Huntington's disease, multiple sclerosis, amyotrophic lateral sclerosis, neurodegeneration due to acute and/or chronic viral or bacterial infections and multiinfarct dementia.

They can moreover be employed in medicaments for the treatment of states of pain, emesis, nausea, glaucoma, asthma, anorexia, convulsions, rheumatism, sedation and mobility disorders.

The substances according to the invention are also suitable for the treatment of disorders which are caused by bacterial and/or viral infections and are based on direct and/or indirect alterations of the immune system or on dysregulations with participation of the immune system, such as, for example, in local or systemic autoimmune diseases (e.g. lupus erythematosus in all its variants), inflammatory and/or autoimmunological diseases of the joints (e.g. primary chronic polyarthritis, trauma-related inflammation), inflammatory and/or autoimmunologically related diseases of the bone and muscle apparatus, inflammatory and/or autoimmunologically related pathogenic processes of the internal organs (e.g. Crohn's disease, glomerulonephritis) and of the external organs (e.g. allergic reactions due to aerogenic intake of antigens) and of the central nervous system (e.g. multiple sclerosis, Alzheimer's disease, psychiatric disorders) as well as of the sense organs, primary and/or secondary and/or autoimmunological disorders of the haematogenic system and of the immune system (e.g. rejection reactions, AIDS) themselves, and also in skin disorders of inflammatory and/or immunological origin in humans and animals. These substances furthermore act on the indirect symptoms of these disorders such as, for example, pain.

Their use for the treatment of pain, spasticity, cerebral ischaemias and craniocerebral trauma is preferred.

To determine the solubility, a precipitation method was used:

10 mg of the test substance are completely dissolved in 50 µl of DMSO (stock solution). From this solution, 20 µl are added to 2000 µl of physiological saline. This solution in turn is shaken at 25° C. in a Thermomixer Comfort (from Eppendorf) at 1400 rpm for 1 hour, for equilibration. The precipitated fractions of the test substance are centrifuged off at 14,000 rpm for 5 min, using a Biofuge 15 from Heraeus. 1300 µl of the supernatant are again centrifuged using a Microfuge from Beckmann, at 45,000 rpm=125,000 g. 10 µl of this centrifugation supernatant are then diluted with 1000 µl of DMSO, and this solution is measured by HPLC. (Hewlett Packard 1090, method: gradient of 100% PBS buffer pH=4 over 15 min to 10% buffer/90% acetonitrile, column: RP18) The measured peak area of the HPLC determination is converted into the substance concentration using a calibration curve. For the calibration curve, 20 µl of the stock solution are successively diluted with DMSO in such a manner that 5 concentrations of from 2.5 mg/l to 2000 mg/l are obtained. These solutions are likewise measured by HPLC (method see above) and the peak areas are plotted against the concentrations.

CB1—Luciferase Reporter Gene Test

1. Cloning of the Rat Cannabinoid Receptor CB1

Total RNA from rat brain (the tissue was taken from freshly killed animals and shock-frozen in liquid nitrogen) was isolated by acidic guanidinium thiocyanate/phenol/chloroform extraction (J. Biol. Chem. 1979, 18, 5294) and converted into cDNA by means of reverse transcriptase and random primers (in each case from Invitrogen). The polymerase chain reaction (PCR, conditions: 4 min 94° C., 1H; 1 min 94° C.; 2 min 53° C.; 1 min 72° C., 50 cycles; 1 min 94° C., 2 min 53° C., 4 min 72° C., 1H) was carried out in a Perkin Elmer thermocycler using the enzyme Taq polymerase (Perkin Elmer); the oligonucleotide primers employed (bases 99 to 122: 5'63', "down"; 1556–1575: 3'75', "up") were derived from the published sequence of the rat cannabinoid receptor (Nature 1990, 346, 561) and were synthesized on a DNA synthesizer, model 1380 from Applied Biosystems. One part of the PCR reaction was separated in a 1% strength agarose gel in 1H TBE buffer and then stained with ethidium bromide, only one band having the expected length being visible (approximately 1.5 kb). This PCR product was subcloned into the TA cloning vector (Invitrogen) and the nucleotide sequence of the insert was determined by the dideoxynucleotide chain termination reaction using T7DNA polymerase (Sequenase, USA/Amersham). The insert has a length of 1477 base pairs and contains an open reading frame of 1419 base pairs which corresponds to a protein of 473 amino acids. The number of base pairs, the position of the open reading frame and the number of amino acids agree with the published sequence. Computer analyses were carried out with the aid of the GCG software suite (Genetic Computer Group). The cDNA insert was subcloned into the expression vector pRc/CMV (Invitrogen) after partial digestion with HindIII and NotI (Biolabs). This construct (plasmid CMV-RH) was employed for transfection experiments.

2. Stable Transfection of the CHOluc9 Reporter Cells

CHOluc9 cells were cultured in 50% Dulbecco's modified Eagle medium/50% F-12 (DMEM/F12) which contained 10% foetal calf serum (FCS). Transfections were prepared in 6-well plates. 7.5 µg of Qiagen-purified CMV-RH plasmid DNA were added per 105 cells with the DOTAP transfection system, corresponding to the experimental protocol of the manufacturer (Boehringer Mannheim). Transfected cells were selected using 1 mg/ml G418 and individual clones were obtained by limiting dilution in 96-well plates. Cell lines which express the cannabinoid receptor were identified for the inhibition of reporter gene expression after incubation with the cannabinoid receptor agonist, WIN-55,212-2, in the presence of forskolin. Several stably transfected and subcloned cell lines were further characterized by means of RT-PCR, as described under 1.

3. Test Optimization and Pharmacological Characterization of the CHOCB1 Reporter Cell Line With the aim of high sensitivity and reproducibility, low variance and high suitability for carrying out on the robotic system, the luciferase test was optimized by variation of several test parameters, such as, for example, cell density, duration of the growth phase and the test incubation, forskolin concentration, medium composition. The following test protocol was used for pharmacological characterization of the cells and for robot-assisted substance screening: the stock cultures were cultured in 50% Dulbecco's modified Eagle medium/50% F-12 (DMEM/F12) with 10% FCS at 37° C. under 10% $CO_2$ and in each case split 1:10 after 2 to 3 days. Test cultures were inoculated into 96-well plates at 5000 cells per well and cultured at 37° C. for 70 hours. The cultures were then carefully washed with phosphate-buffered saline and reconstituted using serum-free ultra-CHO medium (Bio-Whittaker). The substances dissolved in DMSO were diluted 1H in medium and pipetted into the test cultures (maximum DMSO final concentration in the test batch: 0.5%). 20 minutes later, forskolin was added and the cultures were then incubated at 37° C. in an incubator for 3 hours. The supernatants were then removed and the cells were lysed by addition of 25 µl of lysis reagent (25 mM triphosphate, pH 7.8 with 2 mM DTT, 10% glycerol, 3% TritonX100). Directly after this, luciferase substrate solution (2.5 mM ATP, 0.5 mM luciferin, 0.1 mM coenzyme A, 10 mM tricine, 1.35 mM MgSO4, 15 mM DTT, pH 7.8) was added, the mixture was briefly shaken and the luciferase activity was measured using a Hamamatzu camera system.

For inactivation of $G_i$ proteins, the test cultures were treated with 5 ng/ml (final conc.) of Pertussis toxin for 16 hours before the test.

The $IC_{50}$ values were calculated using the GraphPadPrism program (Hill equation, specific: one-site competition).

Activity in the rat CB1 receptor luciferase receptor gene test

| Example | $IC_{50}$ (nmol/l) |
|---------|--------------------|
| 1       | 0.55               | hCB2—Luciferase Reporter Gene Test

CHOluc9 cells were stably transfected using the human CB2 receptor. Transfection, clone selection and test development were carried out analogously to the studies using the rat CB1 receptor. The following test protocol was used for the pharmacological characterization of the cells and for substance testing:

The stock cultures were cultured in 50% Dulbecco's modified Eagle medium/50% F-12 (DMEM/F12) with 10% FCS at 37° C. under 10% $CO_2$ and in each case split 1:10 after 2 to 3 days. Test cultures were inoculated into 96-well plates at 5000 cells per well in DMEM/F12 medium with 5% FCS and cultured at 37° C. for 70 hours. The medium was then removed from the cultures and replaced by serum-free ultra-CHO medium (Bio-Whittaker). The substances dissolved in DMSO (200H final concentration) were pipetted into the test cultures (maximum DMSO final conc. in the test mixture: 0.5%) and 20 min later forskolin was added. The cultures were then incubated at 37° C. in an incubator for 3.5 hours. The supernatants were then removed and the cells were lysed by addition of 25 µl of lysis reagent (25 mM triphosphate, pH 7.8 with 2 mM DTT, 10% glycerol, 3%

Triton X100). Directly afterwards, 50 μl of luciferase substrate solution, double-concentrated, (5 mM ATP, 1 mM luciferin, 0.2 mM coenzyme A, 10 mM tricine, 1.35 mM $MgSO_4$, 15 mM DTT, pH 7.8) were added, the mixture was briefly shaken, and the luciferase activity was determined using a photomultiplier camera measuring system (Hamamatzu).

The $IC_{50}$ values were calculated using the GraphPad Prism™ program (Hill equation; specific: one-site competition).

Binding Studies on Rat Cortex Membranes

Membrane protein is prepared from different tissues or from cells by standard methods. Buffers, labelled ligand, DMSO or test substance are pipetted together, then 100 μg of protein are added, and the mixture is mixed well and incubated in a waterbath at 30° C. for 60 min. After expiry of the incubation time, the reaction is stopped by addition of ice-cold incubation buffer to each tube. After filtering off, washing is carried out with ¾ ml of incubation buffer. The filters are transferred to minivials and the radioactivity is determined in a scintillation counter.

Inhibition of Glutamate Release

After decapitation of a rat, the skull is opened, and the brain is lifted out and cut along the median fissure. The hippocampus is exposed, separated from the remaining tissue, cut into 350 μm thick sections and incubated at 37° C. in straining vessels for 60 min. Followed by basal value and stimulation 1 with 75 mM KCl (S1), the sections are incubated with test substance and then stimulation is repeated with KCl and test substance (S2). Glutamate concentration of the samples to be investigated is then measured by means of an enzymatic reaction (GLDH) and fluorometric measurement of NADH. By means of a calibration curve, the glutamate content of the sample is determined, and with knowledge of the protein content the glutamate content/mg of protein can be calculated. The ratio S2/S1 is compared; glutamate release inhibitors reduce this ratio in a concentration-dependent manner.

Using the test method below, it is possible to determine the in vitro conversion of the amino acid esters according to the invention into the corresponding alcohols.

Determination of the Stability of Substances in the Blood of Various Species (Rat, Dog, Human)

The Principle of the Method

The test substance is incubated in heparinized blood of each test species. At suitable intervals, aliquots of the mixture are taken and pipetted into an initial charge of acetonitrile. After centrifugation, the supernatant is evaporated and the residue is taken up in a solvent suitable for analysis.

| Material | |
| --- | --- |
| Laboratory centrifuge: | Sigma 4K10 (Sigma Laborzentrifugen, Osterode, Germany) |
| Shaker: | KS500 (Janke und Kunkel, IKA Labortechnik, Staufen, Germany) |
| Waterbath, Thermomix ® | 1442D (Braun-Melsungen, Melsungen, Germany) |
| Evaporation apparatus | BAYER AG |

Procedure

To determine the stability of a test substance in vitro, the substance, which is dissolved in a small volume of a suitable solvent, is incubated in a concentration of, for example, 2 μg/ml in 5 ml of blood at 37° C. for 5 hours. At suitable intervals, 100 μl of the mixture are pipetted into 500 μl of the initial charge of acetonitrile and mixed. Following centrifugation at 3000 rpm, the supernatant is removed and evaporated to dryness in a waterbath at 40° C. The residue is taken up in a solvent suitable for analysis.

| | |
| --- | --- |
| Solvent: | 10 μl of EtOH/5 ml of blood |
| Shaker speed: | 250 rpm |
| Centrifugation | 3000 rpm |
| Centrifugation time: | 10 min |
| Blood volume: | 5 ml |
| Blood aliquots: | 100 μl |
| Incubation times: | 0, 2, 5, 10, 15, 30, 45 minutes, 1, 2, 3, 5 hours |

Pharmacokinetics of the Substances in the Rat

1. Intravenous Infusion

The substance is, via a lateral tail vein, infused directly into the blood stream via a venous catheter (Introcan®, 22G1, Braun, Melsungen, Germany). A calibrated 10 ml syringe is used for accurate administration of the selected dose and the volume. For the infusion, pump No. 540210 from TSE, Bad Homburg, FRG, is used.

2. Drawing of Samples and Work-up

Blood and Plasma

Blood samples of animals fitted with a catheter (Vena jugularis) are collected in heparinized tubes. The blood is centrifuged and the plasma is prepared in a suitable manner for analysis. Until analysis, the plasma is stored at <−15° C.

Pharmacokinetics of the Substances in the Dog

1. Intravenous Infusion

Following cannulation of a surface vein of the foreleg or hindleg, the substance is infused directly into the blood stream. The venous catheter (for example Introcan® 20 G/1¼, B. Braun, Melsungen, Germany) is linked with a calibrated syringe, which is attached to the infusion pump.

2. Taking of Samples and Work-up

Blood and Plasma

Blood samples are taken by puncture of a surface vein of the foreleg or hindleg or a jugular vein. The extremity used for the infusion is not used for taking blood samples. The blood is centrifuged and the plasma is stored at <−15° C. until analysis.

Hypothermia

1. Agonism Testing:

Five minutes after determination of the basal body temperature via an oesophageal temperature probe, the test substance is administered (i.v.). A control group receives only the solvent of the test substances, likewise i.v. The body temperature is measured 7.5, 15, 30 and 60 minutes after i.v. administration. The group size per dose is 5–7 animals (rats).

2. Antagonism Testing:

The specific CB1 antagonist SR 141716A, or, to the control group, only the solvent (Solutol/0.9% NaCl), is administered intraperitoneally 60 minutes before administration of test substance. The basal body temperature is measured five minutes before administration of SR 141716A via oesophageal temperature probe. The further procedure corresponds to the "agonism testing" method. The group size per dose is 5–7 animals (rats).

Permanent Focal Cerebral Ischaemia in the Rat (MCA-O)

Under isoflurane anaesthesia, the median cerebral artery is exposed on one side and the latter and its side branches are irreversibly sealed by means of electrocoagulation. As a result of the intervention a cerebral infarct is formed. During the operation, the body temperature of the animal is kept at 37° C. After wound closure and wearing off of the anaesthesia, the animals are again released into their cage. The administration of substance is carried out according to different time schemes and via different administration routes (i.v., i.p.) after occlusion. The infarct size is determined after 7 days. To do this, the brain is removed, worked up histologically and the infarct volume is determined with the aid of a computer-assisted analysis system.

Subdural Haematoma in the Rat (SDH)

Under anaesthesia, the animals are injected with their own blood subdurally on one side. An infarct is formed under the haematoma. Substance administration is carried out according to different time schemes and via different administration routes (i.v., i.p.). The determination of the infarct size is carried out as described in the model of permanent focal ischaemia in the rat (MCA-O).

The novel active compounds can be converted in a known manner into the customary formulations, such as tablets, coated tablets, pills, granules, aerosols, syrups, emulsions, suspensions and solutions, using inert non-toxic, pharmaceutically suitable excipients or solvents. In this case the therapeutically active compound should in each case be present in a concentration from approximately 0.5 to 90% by weight of the total mixture, i.e. in amounts which are sufficient in order to achieve the dosage range indicated.

The formulations are prepared, for example, by extending the active compounds using solvents and/or excipients, if appropriate using emulsifiers and/or dispersants, it optionally being possible, for example, to use organic solvents as auxiliary solvents if water is used as a diluent.

Administration is carried out in a customary manner, preferably orally, transdermally or parenterally, in particular perlingually or intravenously.

In general, it has proved advantageous in the case of intravenous administration to administer amounts from approximately 0.01 to 10 mg/kg, preferably approximately 0.1 to 10 mg/kg, of body weight to achieve effective results.

In spite of this, if appropriate it may be necessary to depart from the amounts mentioned, namely depending on the body weight or on the type of administration route, on individual behaviour towards the medicament, the manner of its formulation and the time or interval at which administration takes place. Thus in some cases it may be adequate to manage with less than the abovementioned minimum amounts, while in other cases the upper limit mentioned has to be exceeded. In the case of the administration of relatively large amounts, it may be advisable to divide these into several individual doses over the course of the day.

Starting Materials

EXAMPLE 1A 4,4,4-Trifluorobutyl Thiocyanate

At 0° C., a stirred solution of 4,4,4-trifluorobutanol (35 g; 0.027 mol) and triethylamine (28.3 g; 0.280 mol) in 200 ml of dichloromethane was admixed dropwise with a solution of methanesulphonyl chloride (32.1 g; 0.280 mol) in 100 ml of dichloromethane. After the addition had ended, the mixture was stirred for a further 30 min and then poured on ice, and the phases were then separated. The organic phase was dried over magnesium sulphate and concentrated under reduced pressure. This gave 55 g of crude 4,4,4-trifluorobutyl-methanesulphonate as an orange oil.

The mesylate (55 g) and sodium thiocyanate (30.6 g; 0.30 mol) were boiled under reflux in acetone (300 ml) for 6 h. After cooling to room temperature, the mixture was poured on ice, the phases were separated and the organic phase was dried over magnesium sulphate. Filtration and concentration under reduced pressure gave 41 g (89% of theory) of 4,4,4-trifluorobutyl thiocyanate as an oil.

$^{19}$F-NMR (376 MHz, CDCl$_3$; CFCl$_3$ d [ppm]: −66.3

$^1$H-NMR (400 MHz, CDCl$_3$, TMS) d [ppm]: 2.15 (m, 2H); 2.3 (m, 2H); 3.05 (t, J=7.1 Hz, 2H)

EXAMPLE 2A 4,4,4-Trifluorobutanesulphonyl Chloride

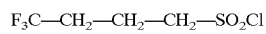

At from 20° C. to 40° C., chlorine was introduced into a solution of Example 1 A (40 g; 0.236 mol) in aqueous acetic acid (150 ml of acetic acid and 70 ml of water), and the progress of the reaction was monitored by gas chromatography. After completion of the chlorination, excess chlorine was flushed out by passing through a stream of nitrogen, 200 ml of water were added and the reaction mixture was extracted repeatedly with dichloromethane. The combined organic phases were dried over magnesium sulphate, the magnesium sulphate was filtered off and the filtrate was concentrated under reduced pressure. This gave 44 g (89% of theory) of 4,4,4-trifluorobutanesulphonyl chloride as a yellow oil.

$^{19}$F-NMR (376 MHz, CDCl$_3$; CFCl$_3$) d [ppm]: −66.65 (t, J=10 Hz)

$^1$H-NMR (400 MHz, CDCl$_3$, TMS) d [ppm]: 3.8 (m, 2H); 2.35 (m, 4H)

EXAMPLE 3A

7-Hydroxy-2-hydroxymethyl-benzofuran

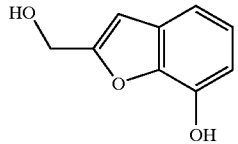

A solution of 2-hydroxymethyl-7-methoxy-benzofuran (2.94 g; 16.5 mmol; preparation WO 96 20925) in N-methylpyrrolidone (45 ml) is admixed with anhydrous sodium sulphide (6.89 g; 88.3 mmol) and stirred under argon at 160° C. for 48 h. After cooling, the reaction mixture is poured into 300 ml of 2 N HCl and extracted with ethyl acetate (3×150 ml). The combined organic phases are dried (Na$_2$SO$_4$) and concentrated under reduced pressure. The residue is chromatographed over silica gel using toluene/ethyl acetate (1:1).

Yield: 1.83 g (68% of theory)

M.p.: 136–138° C.

R$_f$=0.36 (toluene/ethyl acetate=1:1)

MS (DCI/NH$_3$): m/z=182 (M+NH$_4$)

EXAMPLE 4A

2-Hydroxymethyl-7-(3-methoxyphenyloxy)-benzofuran

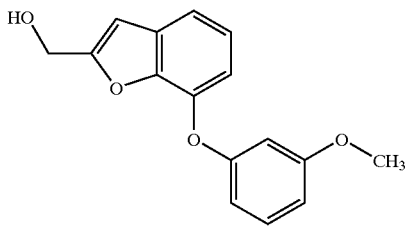

Example 3A (1.85 g; 11.3 mmol) 3-bromoanisol (12.65 g; 67.6 mmol) and potassium carbonate (3.12 g; 22.5 mmol) are initially charged under argon in pyridine (60 ml) and heated with stirring to 140° C. After addition of copper-(I) iodide (2.15 g; 11.3 mmol), the mixture is stirred at 140° C. for 27 h. After cooling, the mixture is filtered through kieselguhr, washed with dichloromethane (150 ml) and concentrated under reduced pressure. The residue is taken up in ethyl acetate (200 ml) and water (200 ml) and the resulting precipitate is filtered off with suction and discarded. After phase-separation, the organic phase is washed with 1 N HCl (2×200 ml) and water (200 ml), dried ($Na_2SO_4$) and concentrated under reduced pressure. The residue is chromatographed over silica gel using toluene/ethyl acetate (5:1).

Yield: 2.05 g (67% of theory)

$R_f$=0.30 (toluene/ethyl acetate=5:1)

MS ($DCI/NH_3$): m/z=288 (M+$NH_4$)

EXAMPLE 5A

2-Hydroxymethyl-7-(3-hydroxyphenyloxy)-benzofuran

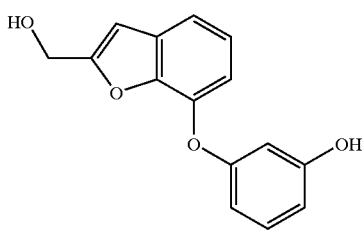

The preparation was carried out analogously to the preparation of Example 3A starting from Example 4A (1.95 g; 7.21 mmol).

Yield: 0.465 g (25% of theory)

$R_f$=0.47 (toluene/ethyl acetate=1:1)

MS (ESI): m/z=279 (M+Na)

EXAMPLE 6A 3-(2,3-Dimethylphenyloxy)-anisole

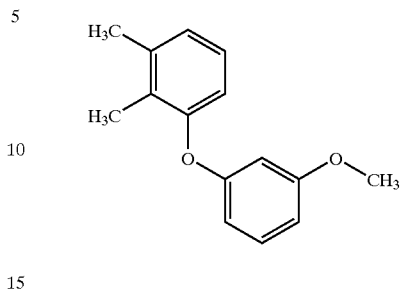

Under argon, 2,3-dimethyl-1-bromobenzene (80.0 g; 0.432 mol), 3-methoxyphenol (107.3 g; 0.865 mol) and potassium carbonate (119.5 g; 0.865 mol) are initially charged in pyridine (350 ml) under argon and heated to 100° C. Copper-(II) oxide (51.6 g; 0.648 mol) are added, and the mixture is then stirred at 140° C. After 15 h and 40 h, more 2,3-dimethyl-1-bromobenzene is added (80.0 g; 0.432 mol after 15 h and 66.0 g; 0.357 mol after 40 h). After 64 h, the mixture is concentrated under reduced pressure, and the residue is taken up in ethyl acetate and adjusted to pH 2–3 using half-concentrated hydrochloric acid. After phase separation, the organic phase is washed with sat. NaCl solution, dried ($Na_2SO_4$) and concentrated under reduced pressure using a rotary evaporator. The residue is chromatographed over silica gel using tol: EA=5:1.

Yield: 94.9 g (36% of theory)

$R_f$=0.76 (toluene)

MS ($DCI/NH_3$): m/z=246 (M+$NH_4$)

EXAMPLE 7A 3-(2,3-Dimethylphenyloxy)-phenol

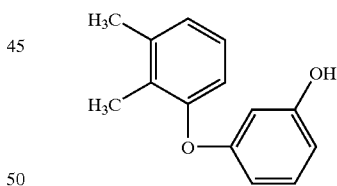

Example 6A (109.6 g; 480 mmol) is initially charged in 48% aqueous hydrogen bromide (900 ml) and acetic acid (1500 ml) and stirred under reflux overnight. The mixture is then concentrated under reduced pressure and the residue is taken up in water and extracted three times with ethyl acetate. The combined organic phases are washed twice with water, dried ($MgSO_4$) and concentrated under reduced pressure. The residue is chromatographed over silica gel using toluene:EA (10:1).

Yield: 86.5 g (83% of theory)

$R_f$=0.15 (toluene)

MS (ESI): m/z=215 (M+H)

EXAMPLE 8A 3-(2,3-Dimethylphenyloxy)-phenyl 4,4,4-trifluoro-1-butanesulphonate

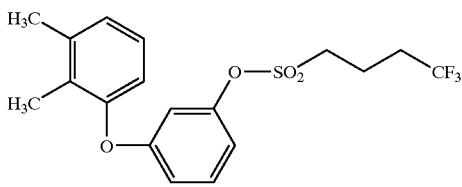

The preparation was carried out analogously to the preparation of Example 1 starting from Example 7A (4.54 g; 21.2 mmol).

Yield: 7.80 g (95% of theory)

$R_f$=0.51 (toluene)

MS (DCI/NH$_3$): m/z=406 (M+NH$_4$)

EXAMPLE 9A 3-(2-Bromomethyl-3-dibromomethylphenyloxy)-phenyl 4,4,4-trifluoro-1-butanesulphonate

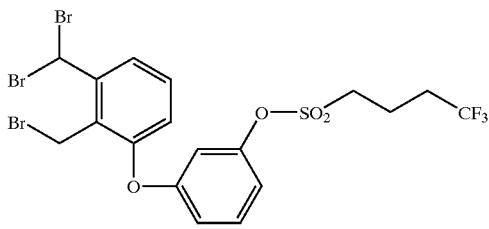

A solution of Example 8A (6.76 g, 17.4 mmol) in carbon tetrachloride (150 ml) is admixed with N-bromosuccinimide (6.50 g; 36.5 mmol), heated at reflux and, with stirring, irradiated with a 300 W lamp for 5 h. After cooling, precipitated succinimide is filtered off with suction, and the filtrate is concentrated under reduced pressure. The residue is chromatographed over silica gel using toluene. This gives a mixture (about 5:1) of 3-(2,3-bis-bromomethylphenyloxy)-phenyl 4,4,4-trifluoro-1-butanesulphonate and the desired product (HPLC, Nucleosil C18, acetonitrile, 0.01 M H$_3$PO$_4$). The resulting mixture was used further without further purification.

EXAMPLE 10A (R,S)-3-(1-Bromo-2,2-bis-methoxycarbonyl-indanyl-4-oxy)-phenyl 4,4,4-trifluoro-1-butanesulphonate

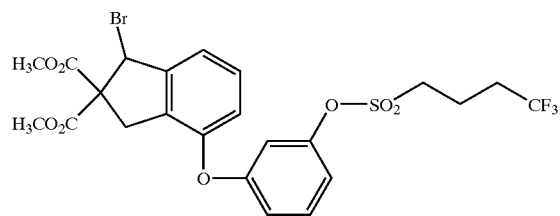

The about 5:1 mixture, obtained in Example 9A, of 3-(2,3-bis-bromomethylphenyloxy)-phenyl 4,4,4-trifluoro-1-butanesulphonate and 3-(2-bromomethyl-3-dibromo-methylphenyloxy)-phenyl 4,4,4-trifluoro-1-butanesulphonate (6.00 g) is dissolved in 2-butanone (150 ml). Dimethyl malonate (1.136 g; 8.6 mmol) and potassium carbonate (5.35 g; 38.7 mmol) are added, and the reaction mixture is then stirred under reflux overnight. After cooling, the undissolved salts are filtered off with suction and the filtrate is concentrated under reduced pressure. The residue is chromatographed over silica gel using toluene:ethyl acetate (20:1). The main product is 3-(2,2-bis-methoxycarbonyl-indanyl-4-oxy)-phenyl 4,4,4-trifluoro-1-butanesulphonate (1.95 g; 35% of theory, erR$_f$=0.45 (toluene/ethyl acetate=20:1)).

Yield of Example 10A: 0.82 g (16% of theory)

$R_f$=0.52 (toluene/ethyl acetate=20:1)

MS (DCI/NH$_3$): m/z=612, 614 (M+NH$_4$)

PREPARATION EXAMPLES

Example 1

2-Hydroxymethyl-7-[3-(4,4,4-trifluorobutyl-1-sulphonyloxy)phenyl-1-oxy]-benzofuran

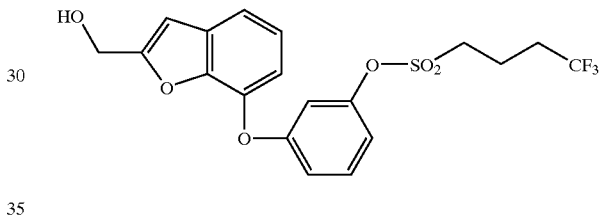

At RT and under argon, a solution of Example 5A (0.382 g; 1.49 mmol) in dichloromethane (10 ml) is admixed with Example 2A (0.314 g; 1.49 mmol) and stirred at RT for 1 h. Triethylamine (0.151 g; 1.49 mmol) is added, and the mixture is then stirred at RT for another 48 h. The reaction mixture is then washed with water (2×50 ml), dried (Na$_2$SO$_4$) and concentrated under reduced pressure. The residue is chromatographed over silica gel using toluene/ethyl acetate (10:1).

Yield: 0.292 g (45% of theory)

$R_f$=0.67 (toluene/ethyl acetate=1:1)

MS (DCI/NH$_3$): m/z=448 (M+NH$_4$)

Examples 2 and 3

3-(2-Methoxycarbonyl-indenyl-4-oxy)-phenyl 4,4,4-trifluoro-1-butanesulphonate and 3-(2-Methoxycarbonyl-indenyl-7-oxy)-phenyl 4,4,4-trifluoro-1-butanesulphonate

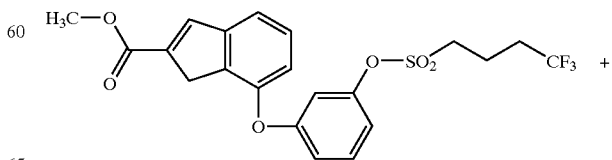

Example 2

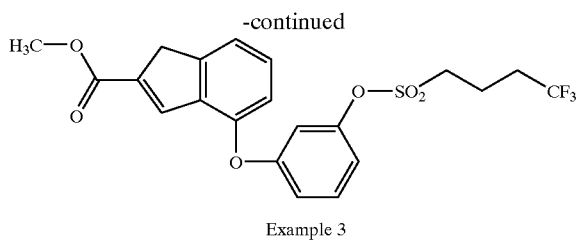

Example 3

A solution of Example 10A (0.904 g; 1.52 mmol) in acetic acid (9 ml) and hydrogen bromide, 48% strength in water (3 ml) is stirred under reflux for 24 h.

The mixture is then concentrated under reduced pressure and the residue is taken up in ethyl acetate (50 ml) and washed with water (3×50 ml). The combined organic phases are dried over $Na_2SO_4$ and concentrated under reduced pressure. The residue is dissolved in dichloromethane (8 ml) and, at −10° C. and under argon, admixed with methanol (0.243 g, 7.60 mmol), N-ethyl-N'-3-(dimethylaminopropyl)-carbodiimide hydrochloride (0.321 g; 1.67 mmol) and 4-dimethylaminopyridine (0.019 g; 0.15 mmol) and stirred at RT overnight. The mixture is washed with water, twice with sat. aqueous $NaHCO_3$ solution and with water, dried ($Na_2SO_4$) and concentrated under reduced pressure. The residue is chromatographed over silica gel using toluene/ethyl acetate (10:1).

Yield: 0.357 mg (51% of theory of an about 2:1 mixture of Example 2 and 3)

$R_f$=0.40 (toluene/ethyl acetate=10:1)

$^1$H-NMR (CDCl$_3$): δ=7.72 (t, J=0.5 Hz, 1-CH of the indenyl substituent of Example 2), 7.69 (t, J=0.5 Hz, 1-CH of the indenyl substituent of Example 3) MS(DCI/NH$_3$): m/z=474 (M+NH$_4$)

Examples 4 and 5

3-(2-Hydroxymethyl-indenyl-4-oxy)-phenyl 4,4,4-Trifluoro-1-butanesulphonate (Example 4) and 3-(2-Hydroxymethyl-indenyl-7-oxy)-phenyl 4,4,4-trifluoro-1-butanesulphonate (Example 5)

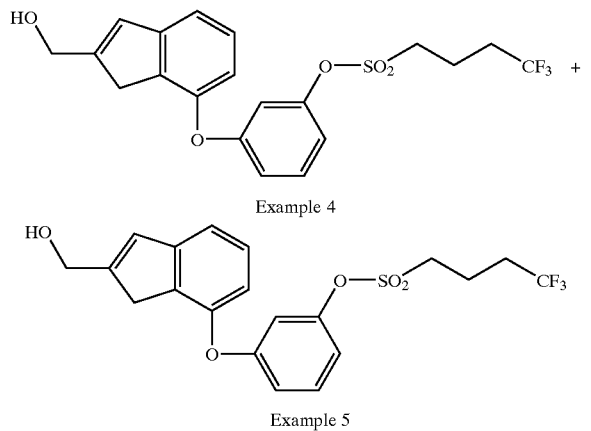

At −70° C. and under argon, diisobutylaluminium hydride, 1 M in dichloromethane (1.55 ml; 1.55 mmol) is added dropwise to a solution of the 2:1 mixture of Examples 2 and 3 (283 mg, 0.62 mmol) in dichloromethane (10 ml), and the mixture is stirred at −70° C. for 45 min. The mixture is then warmed to −10° C. and admixed with methanol (1 ml) and an sat. aqueous sodium potassium tartrate solution (20 ml). The aqueous phase is extracted with dichloromethane (2×50 ml) and the combined organic phases are dried ($Na_2SO_4$) and concentrated under reduced pressure. the residue is chromatographed over silica gel using toluene/ethyl acetate=2:1. This gives an about 2:1 mixture of Examples 4 and 5 ($R_f$=0.56, toluene/ethyl acetate=1:1, MS (DCI/NH$_3$): m/z=446 (M+NH$_4$)). This mixture (120 mg) is separated by preparative HPLC (Daicel Chiralpak AD, 10 μm, 250×20 mm, flow rate 6 ml/min, mobile phase 35% n-heptane and 65% ethanol, detection 260 nM, T=40° C.) into the regioisomers Example 4 and Example 5.

Example 4

Yield: 54 mg

Retention time: 4.01 min $^1$H-NMR (D6-DMSO): δ=3.2 (2H; 3-CH$_2$ of the indanyl substituent), 6.71 (1H; 1-CH of indanyl) ppm Example 5

Yield: 32 mg

Retention time: 4.54 min $^1$H-NMR (D6-DMSO): δ=3.48 (2H; 3-CH$_2$ of the indanyl substituent), 6.50 (1H; 1-CH of the indanyl substituent)

What is claimed is:

1. Compounds of the general formula (I)

$$R^1\text{-A-D-E-G-L-}R^2 \qquad (I)$$

in which $R^1$ represents a radical of the formula

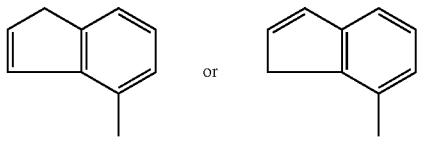

in which the ring systems listed above are optionally substituted, optionally geminally, by one or more identical or different substituents selected from the group consisting of:

halogen, carboxyl, hydroxyl, phenyl, ($C_1$–$C_6$)-alkoxy, ($C_1$–$C_6$)-alkoxycarbonyl, ($C_1$–$C_8$)-alkyl, which for its part may be substituted by halogen, ($C_1$–$C_6$)-alkylsulphonyloxy, azide, amino, mono($C_1$–$C_6$)-alkylamino, di($C_1$–$C_6$)-alkylamino or hydroxyl, a group of the formula —(CO)$_b$–NR$^4$R$^5$, in which b represents a number 0 or 1, $R^4$ and $R^5$ are identical or different and independently of one another represent hydrogen, phenyl, ($C_1$–$C_6$)-acyl, cyclo($C_4$–$C_7$)-acyl benzoyl or ($C_1$–$C_6$)-alkyl, which is optionally substituted by amino, mono ($C_1$–$C_6$)-alkylamino, di($C_1$–$C_6$)-alkylamino, or $R^4$ and $R^5$ together with the nitrogen atom form a 5- or 6-membered saturated heterocycle which may optionally contain one or more further heteroatom(s) from the group consisting of S and O and/or one or more radical(s) of the formula —NR$^8$, in which $R^8$ represents hydrogen, ($C_1$–$C_6$)-alkyl or ($C_1$–$C_6$)-acyl, and
a group of the formula —NR$^6$—SO$_2$—R$^7$
in which
and
R$^6$ represents hydrogen, phenyl, (C$_1$–C$_6$)-alkyl or (C$_1$–C$_6$)-acyl,
R$^7$ represents phenyl or (C$_1$–C$_6$)-alkyl,
and a radical of the formula

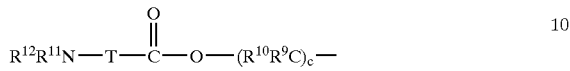

in which
c represents a number 1, 2, 3, 4, 5 or 6,
R$^9$ and R$^{10}$ are identical or different and represent hydrogen or (C$_1$–C$_6$)-alkyl,
T represents a radical of the formula —(CH$_2$)$_d$—,
in which
d represents a number 1, 2, 3, 4, 5 or 6,
or
T represents a moiety of an amino acid radical of the formula

in which
R$^{13}$ and R$^{14}$ are identical or different and represent hydrogen or methyl,
or
R$^{13}$ represents hydrogen or methyl
and
R$^{14}$ represents (C$_3$–C$_8$)-cycloalkyl or (C$_6$–C$_{10}$)-aryl or hydrogen,
or
(C$_1$–C$_8$)-alkyl,
where the (C$_1$–C$_8$)-alkyl is optionally substituted by methlythio, hydroxyl, mercapto, guanidyl or by a group of the formula —NR$^{15}$R$^{16}$ or —NR$^{17}$—OC—,
in which
R$^{15}$ and R$^{16}$ independently of one another represent hydrogen, (C$_1$–C$_8$)-alkyl or phenyl
and
R$^{17}$ represents hydroxyl, benzyloxy, (C$_1$–C$_8$)-alkoxy or the group —NR$^{15}$R$^{16}$ listed above,
or the (C$_1$–C$_8$)-alkyl is optionally substituted by (C$_3$–C$_6$)-cycloalkyl or phenyl, which for its part is substituted by hydroxyl, halogen or (C$_1$–C$_6$)-alkoxy or amino,
or the (C$_1$–C$_8$)-alkyl is optionally substituted by imidazolyl or indolyl, in which the corresponding —NH functions are optionally protected by (C$_2$–C$_6$)-alkyl or by an amino protective group,
R$^{11}$ and R$^{12}$ are identical or different and represent hydrogen, (C$_1$–C$_6$)-alkyl or a typical amino protective group,
or
R$^{11}$ and R$^{12}$ together with the nitrogen atom form a 5-to 6-membered saturated heterocycle, which may optionally contain a further heteroatom from the group consisting of S and O or a radical of the formula —NR$^{18}$,
in which
R$^{18}$ represents hydrogen, (C$_1$–C$_6$)-alkyl or phenyl,
A and E D represents an oxygen atom or represents a radical of the formula —S(O)$_e$— or —N(R$^{19}$)—,
in which
e represents a number 0, 1 or 2,
R$^{19}$ represents hydrogen, (C$_1$–C$_6$)-alkyl or (C$_1$–C$_6$)-acyl,
G represents doubly attached (C$_6$–C$_{10}$)-aryl which is optionally substituted by one or more identical or different substituents selected from the group consisting of:
hydroxyl, trifluoromethyl, carboxyl, halogen, (C$_1$–C$_6$)-alkyl, hydroxy(C$_1$–C$_6$)-alkyl, (C$_1$–C$_6$)-alkoxy, (C$_1$–C$_6$)-alkoxycarbonyl, and groups of the formulae —CO—O—(CH$_2$)$_f$—NR$^{20}$R$^{21}$, —NR$^{22}$—SO$_2$R$^{23}$, —(CH$_2$)$_g$—(CO)$_h$—NR$^{24}$R$^{25}$ and —OR$^{26}$,
in which
f represents a number 1, 2, 3 or 4,
g and h are identical or different and represent a number 0 or 1,
R$^{20}$ and R$^{21}$ have the meaning of R$^4$ and R$^5$ given above,
R$^{22}$ has the meaning of R$^6$ given above,
R$^{23}$ has the meaning of R$^7$ given above,
R$^{24}$ and R$^{25}$ have the meaning of R$^4$ and R$^5$ given above,
or independently of one another represent a radical of the formula
—(CH$_2$)$_i$—NR$^{27}$R$^{28}$,
in which
i represents a number 1, 2, 3 or 4,
and
R$^{27}$ R$^{28}$ have the meaning of R$^4$ and R$^5$ given above,
R$^{26}$ represents (C$_6$–C$_{10}$)-aryl,
L represents a radical of the formula,

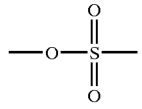

where the left-hand side of the radicals is attached to G,
R$^2$ represents (C$_6$–C$_{10}$)-aryl or represents a 5- to 7-membered saturated or aromatic heterocycle having up to 3 heteroatoms from the group consisting of S, N and O, which are optionally substituted by one or more identical or different substituents selected from the group consisting of:
halogen, trifluoromethyl, nitro, amino and (C$_1$–C$_6$)-alkyl,
or
represents the radical of the formula

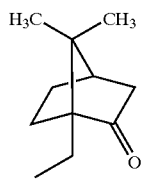

or morpholine, or represents C$_3$–C$_8$-cycloalkyl, or
represents (C$_1$–C$_{12}$)-alkyl, (C$_2$–C$_{12}$)-alkenyl or (C$_2$–C$_{12}$)-alkinyl, which are optionally substituted by one or more identical or different substituents selected from the group consisting of:

halogen, trifluoromethyl, hydroxyl, cyano, azido, $(C_1-C_6)$-alkoxy, $(C_1-C_6)$-perfluoroalkoxy, partially fluorinated $(C_1-C_6)$-alkoxy, a radical of the formula in which
$R^{38}$ and $R^{39}$ have the meaning of $R^4$ and $R^5$ given above,
phenyl, optionally substituted by one or more identical or different substituents selected from the group consisting of:
halogen, nitro, hydroxyl, $(C_1-C_6)$-alkyl, $(C_1-C_6)$-alkoxy and a group of the formula —$NR^{40}R^{41}$,
in which
$R^{40}$ and $R^{41}$ are identical or different and represent hydrogen or $(C_1-C_6)$-alkyl or $(C_1-C_6)$-acyl,
and a 5- to 6-membered aromatic heterocycle having up to three heteroatoms from the group consisting of S, N and O, optionally substituted by one or more identical or different substituents selected from the group consisting of:
halogen, nitro, hydroxyl, $(C_1-C_6)$-alkyl, $(C_1-C_6)$-alkoxy and a group of the formula —$NR^{40}R^{41}$
in which
$R^{40}$ and $R^{41}$ are as defined above,
or
L and $R^2$ together represent a radical of the formula and pharmaceutically acceptable salts thereof,
with proviso that $R^1$ does not represent an unsubstituted radical.

2. Compounds of the general formula (I) according to claim 1,
$R^1$ represents a radical of the formula or and where the ring systems listed above are optionally substituted, optionally geminally, by one or more identical or different substituents selected from the group consisting of:
fluorine, chlorine, carboxyl, hydroxyl, $(C_1-C_4)$-alkoxy, $(C_1-C_5)$-alkoxycarbonyl or $(C_1-C_6)$-alkyl, which for its part may be substituted by fluorine, chlorine or hydroxyl, and a radical of the formula $$R^{12}R^{11}N-T-\overset{O}{\underset{\|}{C}}-O-(R^{10}R^9C)_c-$$

in which
c represents a number 1, 2, 3, 4, 5 or 6,
$R^9$ and $R^{10}$ are identical or different and represent hydrogen or $(C_1-C_6)$-alkyl,
T represents a radical of the formula —$(CH_2)_d$—,
in which
d represents a number 1, 2, 3, 4, 5 or 6,
or
T represents a moiety of an amino acid radical of the formula in which
$R^{13}$ and $R^{14}$ are identical or different and represent hydrogen or $(C_1-C_6)$-alkyl,
or
$R^{13}$ represents hydrogen or methyl
and
$R^{14}$ represents cyclopropyl, cyclopentyl, cyclohexyl, phenyl or hydrogen, or represents $(C_1-C_6)$-alkyl,
where the $(C_1-C_6)$-alkyl is optionally substituted by methylthio, hydroxyl, mercapto, guanidyl or by a group of the formula —$NR^{15}R^{16}$ or —$NR^{17}$—OC—,
in which
$R^{15}R^{16}$ independently of one another represent hydrogen, $(C_1-C_6)$-alkyl or phenyl
and
$R^{17}$ represents hydroxyl, benzyloxy, $(C_1-C_6)$-alkoxy or the group —$NR^{15}R^{16}$ listed above,
or the $(C_1-C_6)$-alkyl is optionally substituted by cyclopropyl, cyclopentyl, cyclohexyl or phenyl, which for its part is substituted by hydroxyl, fluorine, chlorine, bromine or $(C_1-C_4)$-alkoxy or amino,
or
$R^{11}$ and $R^{12}$ are identical or different and represent hydrogen or $(C_1-C_4)$-alkyl,
or
$R^{11}$ and $R^{12}$ together with the nitrogen atom form a morpholinyl piperidinyl or piperazinyl ring,
A and E,
D represents an oxygen atom,
G represents doubly attached phenyl or pyridyl, which are optionally substituted by one or more identical or different substituents selected from the group consisting of:
hydroxyl, trifluoromethyl, carboxyl, halogen, $(C_1-C_4$-alkyl, hydroxy$(C_1-C_4)$alkyl, $(C_1-C_4)$-alkoxy, $(C_1-C_4)$-alkoxycarbonyl and groups of the formulae —CO—O—$(CH_2)_f$—$NR^{20}R^{21}$, —$NR^{22}$—$SO_2R^{23}$, —$(CH_2)g$—$(CO)_h$—$NR^{24}R^{25}$ and $OR^{26}$,
in which
f represents a number 1, 2, 3 or 4,
g and h are identical or different and represent a number 0 or 1,
$R^{20}$ and $R^{21}$ have the meaning of $R^4$ and $R^5$ given above, $R^{22}$ has the meaning of $R^6$ given above,
$R^{23}$ has the meaning of $R^7$ given above,
$R^{24}$ and $R^{25}$ have the meaning of $R^4$ and $R^5$ given above, or independently of one another represent a radical of the formula —$(CH_2)_i$—$NR^{27}R^{28}$,
in which
i represents a number 1, 2 or 3,
and
$R^{27}$ and $R^{28}$ have the meaning of $R^{20}$ and $R^{21}$ given above,
$R^{26}$ represents phenyl or naphthyl,
L represents a radical of the formula

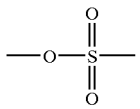

where the left-hand side of the radicals is attached to G,
$R^2$ represents $(C_1–C_{10})$-alkyl which is optionally substituted more identical or different substituents selected from the group consisting of:
fluorine, chlorine, bromine, phenyl, trifluoromethyl, hydroxyl, azido, $(C_1–C_4)$-alkoxy, $(C_1–C_5)$-perfluoroalkoxy or partially fluorinated $(C_1–C_4)$ alkoxy
and pharmaceutically acceptable salts thereof.

3. Compounds of the general formula (I), according to claim 1
in which
$R^1$ represents a radical of the formula

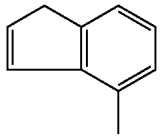 or 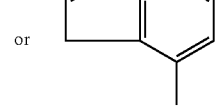

and where the ring systems listed above are optionally substituted by one or more identical or different substituents selected from the group consisting of:
chlorine, fluorine, hydroxyl, $(C_1–C_3)$-alkoxy or $(C_1–C_4)$-alkyl, which for its part may be substituted by hydroxyl,
A and E represent a bond,
D represents an oxygen atom,
G represents doubly attached phenyl which are optionally substituted by one or more identical or different substituents selected from the group consisting of:
hydroxyl, trifluoromethyl, carboxyl, fluorine, chlorine, bromine, $(C_1–C_3)$-alkyl, hydroxy$(C_1–C_3)$ alkyl or $(C_1–C_3)$-alkoxy
L represents a radical of the formula

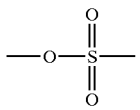

where the left-hand side of the radicals is attached to G,
$R^2$ represents $(C_1–C_8)$-alkyl, which is optionally substituted by one or more identical or different substituents selected from the group consisting of:
fluorine, chlorine, bromine, phenyl, trifluoromethyl or trifluoromethyl-substituted $(C_1–C_4)$-alkoxy,
and pharmaceutically acceptable salts thereof.

4. Compounds of the general formula (I), according to claim 1,
in which
$R^1$ represents a radical of the formula

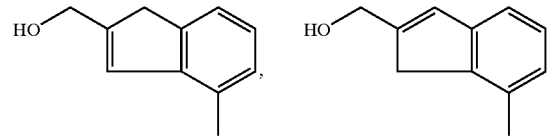

A and E represent bonds,
D represents an oxygen atom,
G represents doubly attached phenyl, which is optionally substituted by fluorine, chlorine or bromine,
L represents a radical of the formula

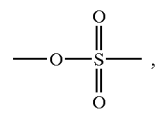

where the left-hand side of the radical is attached to G,
$R^2$ represents $(C_1–C_4)$-alkyl, which is optionally substituted by fluorine or trifluoromethyl,
and pharmaceutically acceptable salts thereof.

5. Compounds selected from the group consisting of

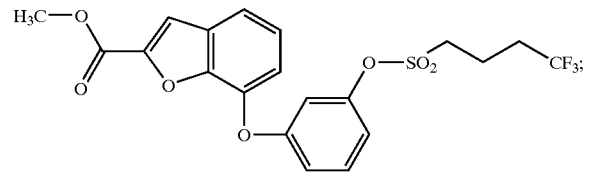

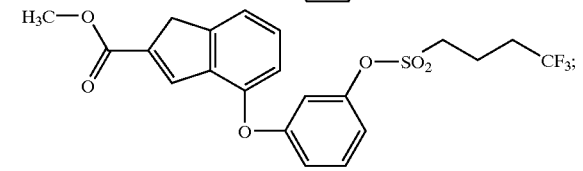

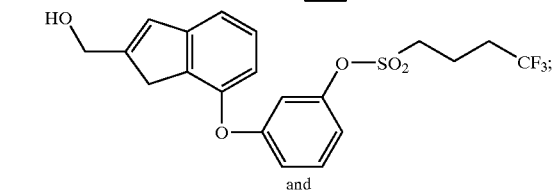

and

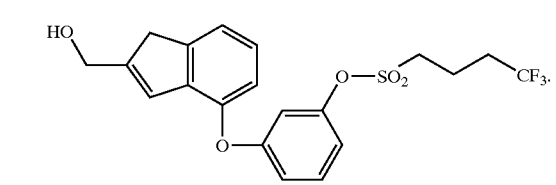

6. A process for preparing novel arylsulphonamides and analogues according to claim 1, characterized in that
[A] compounds of the general formula (IV)

$$R^1\text{-A-D-E-G-M-H} \qquad (II)$$

in which
$R^1$, A, D, E and G have the meaning given in claim 1
and

M represents oxygen or
in which
R⁴² represents hydrogen or (C₁–C₄-alkyl,
are reacted with compounds of the general formula (III)

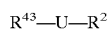 (III)

in which
R² has the meaning given in claim 1,
R⁴³ represents halogen,
U represents a radical of the formula —SO₂—, —SO—, —CO—, —P(O)(OR³⁷)— or a single bond,
in which
R³⁷ has the meaning given in claim 1,
to give compounds of the general formula (Ia)

R¹-A-D-E-G-M-U—R² (Ia)

in which
R¹, A, D, E, G, and R² have the meaning given in claim 1
and M and U have the meaning given above,
in inert solvents,
or
[B] compounds of the general formula (II)
are initially reacted with trialkylsilyl chlorosulphonates, admixed with an acid and then reacted with a chlorinating agent, to give a compound of the general formula (IV)

R¹-A-D-E-G-M-SO₂—Cl (IV)

in which
R¹, A, D, E, and G have the meaning given in claim 1 and M has the meaning given above;
followed by reaction with compounds of the general formula (V)

H—V—R² (V)

in which
R² has the meaning given in claim 1 and
V represents oxygen or nitrogen,
to give compounds of the general formula (Ib)

R¹-A-D-E-G-M-SO₂—V—R² (Ib)

in which
R¹, A, D, E, G, and R² have the meaning given in claim 1
and M and V have the meaning given above,
in inert solvents in the presence of Bzl-NEt₃⁺Cl⁻ and a base,
or
[C] compounds of the general formula (VI)

R¹-A-D'-H (VI)

in which
R¹ and A have the meaning given in claim 1 and
D represents oxygen, sulphur or —N(R¹⁹)— and
R¹⁹ has the meaning given above,
are reacted with compounds of the general formula (VII)

R⁴⁴-E-G-SO₂—NH—R² (VII)

in which
E, G and R² have the meaning given in claim 1 and
R⁴⁴ represents a leaving group,
to give compounds of the general formula (Ic)

R¹-A-D'-E-G-SO₂—NH—R² (Ic)

in which
R¹, A, D', E, G and R² have the meaning given in claim 1, or
[G] compounds of the general formula (Ih)

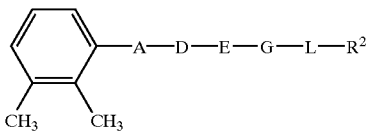 (Ih)

in which
A, D, E, G, L and R² have the meaning given in claim 1,
are converted by free-radical bromination, in an inert solvent into compounds of the general formula (Ii)

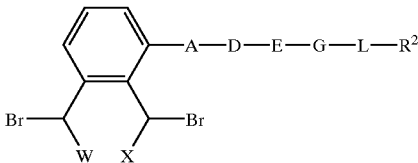 (Ii)

in which
A, D, E, G, L and R² have the meaning given in claim 1,
and one of the substituents W or X represents bromine and the other represents hydrogen,
and subsequently reacted with compounds of the general formula (IX)

CH₂(CO₂R⁵¹)₂ (IX)

in which
R⁵¹ represents (C₁–C₆)-alkyl and
in inert solvents, to give compounds of the general formula (Ij)

R⁵²-A-D-E-G-L-R² (Ij)

in which
A, D, E, G, L and R² have the meaning given in claim 1 and
R⁵² represents a radical of the formula

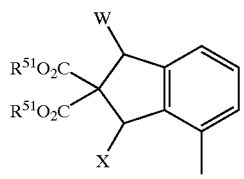

in which
R⁵¹, W and X have the meaning given above, to give compounds of the general formula (X)

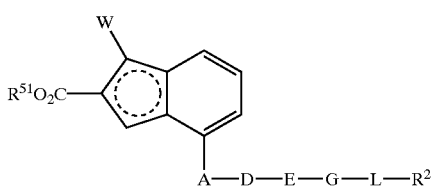

in which
A, D, E, G, L, and $R^2$ have the meaning given in claim 1
and W and $R^{51}$ have the meaning given above,
and finally reduced to the methylhydroxy function,
or
[H] in the case that $R^1$ represents the rings listed above, which are substituted by the radical of the formula

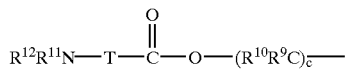

in which
c, T, $R^9$, $R^{10}$, $R^{11}$ and $R^{12}$ have the meaning given in claim 1,
compounds of the general formula (XI)

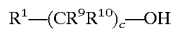 (XI)

are reacted with compounds of the general formula (XII)

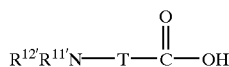 (XII)

in which
T has the meaning given in claim 1,
$R^{11'}$ represents hydrogen
and
$R^{12'}$ represents one of the amino protective groups listed above,
in inert solvents,
and the amino protective group is cleaved off,
and, in the last step, a reduction with $BH_3 \times S(CH_3)_2$ in tetrahydrofuran is carried out,
and, in the case of the pure enantiomers, an HPLC separation is carried,
and, in the case that D=—SO— or —$SO_2$—, an oxidation is carried out on the corresponding thioesters (D=S) by customery methods,
and, in the case of the ammonium compounds, an alkylation is carried out on the corresponding amines.

7. A pharmaceutical composition which comprises, as an active component, at least one compound according to claim 1 in combination with at least one pharmaceutically acceptable essentially non-toxic vehicle or excipient.

8. A method for the treatment of neurodegenerative disorders comprising administering to a mammal an effective amount of a compound according to claim 1.

9. A method for the treatment of cerebral ischaemias and craniocerebral trauma comprising administering to a mammal an effective amount of a compound according to claim 1.

10. A method for the treatment of pain, emesis, nausea, glaucoma, asthma, anorexia, convulsions, rheumatism, sedation, and mobility disorders comprising administering to a mammal an effective amount of a compound according to claim 1.

11. A method for the treatment of bacterial or viral infections, autoimmune diseases, inflammatory or autoimmunologically related diseases of the joints of the bone and muscle apparatus, of the internal organs, of the central nervous system, of the sense organs and of the haematogenic system comprising administering to a mammal an effective amount of a compound according to claim 1.

12. A method for the treatment of migraine and spasticity comprising administering to a mammal an effective amount of a compound according to claim 1.

13. The process of claim 6, wherein said trialkysilyl chlorosulphonate is trimethylsilyl chlorosulphonate and said chlorinating agent is phosphorus pentachloride.

14. The process of claim 6, wherein $R^{43}$ is selected from the group consisting of chlorine and iodine.

15. The process of claim 6, wherein $R^{44}$ is selected from the group consisting of fluorine, chlorine, and bromine.

16. The process of claim 6, wherein said chloroformate is selected from the group consisting of 1-(1-chloro)ethyl chloroformate and methyl chloroformate.

17. The process of claim 6, wherein said alcohol is methanol.

18. The process of claim 6, wherein said reducing agent is sodium cyanoborohydrate.

19. The process of claim 6, wherein $R^{49}$ is a halogen.

20. The process of claim 6, wherein said free-radical bromination is performed using N-bromosuccinimide.

21. The process of claim 6, wherein $R^{12'}$ is tert-butyloxycarbonyl.

22. The process of claim 6, wherein, after removal of the amino protective group, the amino group is reductively alkylated or dialkylated with an aldehyde, ketone, or halide.

23. The process of claim 20, wherein said compound of formula I is esterified.

* * * * *